(12) United States Patent
Sankaran

(10) Patent No.: US 7,985,231 B2
(45) Date of Patent: Jul. 26, 2011

(54) BONE FUSION DEVICE AND METHODS

(75) Inventor: Meera Sankaran, Cupertino, CA (US)

(73) Assignee: Kyphon Sarl, Neuchatal (CH)

( * ) Notice: Subject to any disclaimer, the term of this patent is extended or adjusted under 35 U.S.C. 154(b) by 323 days.

(21) Appl. No.: 11/967,727

(22) Filed: Dec. 31, 2007

(65) Prior Publication Data

US 2009/0171389 A1   Jul. 2, 2009

(51) Int. Cl.
- *A61B 17/58* (2006.01)
- *A61B 17/60* (2006.01)
- *A61F 2/00* (2006.01)

(52) U.S. Cl. .......... 606/105; 606/60; 606/246; 606/249; 623/16.11; 623/17.11; 623/17.16

(58) Field of Classification Search ............. 606/246, 606/61, 248–249, 279, 60, 259, 105; 623/17.11–17.16, 16.11

See application file for complete search history.

(56) References Cited

U.S. PATENT DOCUMENTS

| | | | |
|---|---|---|---|
| 4,422,451 A | | 12/1983 | Kalamchi |
| 5,026,373 A | | 6/1991 | Ray |
| 5,702,395 A | | 12/1997 | Hopf |
| 5,749,916 A | | 5/1998 | Richelsoph |
| 5,976,187 A | | 11/1999 | Richelsoph |
| 6,080,155 A | | 6/2000 | Michelson |
| 6,102,950 A | | 8/2000 | Vacarro |
| 6,126,689 A | * | 10/2000 | Brett .......................... 623/17.16 |
| 6,129,763 A | | 10/2000 | Chauvin |
| 6,159,211 A | * | 12/2000 | Boriani et al. ................ 606/279 |
| 6,290,724 B1 | | 9/2001 | Marino |
| 6,409,766 B1 | | 6/2002 | Brett |
| 6,419,705 B1 | | 7/2002 | Erickson |
| 6,436,140 B1 | | 8/2002 | Liu |
| 6,443,989 B1 | | 9/2002 | Jackson |
| 6,491,695 B1 | | 12/2002 | Roggenbuck |
| 6,582,467 B1 | | 6/2003 | Teitelbaum |
| 6,652,533 B2 | | 11/2003 | O'Neil |
| 6,695,760 B1 | | 2/2004 | Winkler |
| 6,749,613 B1 | | 6/2004 | Conchy |

(Continued)

FOREIGN PATENT DOCUMENTS

EP     1354572 A2    10/2003

(Continued)

OTHER PUBLICATIONS

International Search Report, Nov. 12, 2008.

*Primary Examiner* — Eduardo C Robert
*Assistant Examiner* — Christina Negrelli

(57) ABSTRACT

A bone fusion device can include elongated interlockable segments, each having an engaging surface interlockable with the engaging surface of another segment. The segments can be inserted in between bones one at a time. A device can include an outer expandable component having outer expandable members insertable to a location between bones in an unexpanded configuration and an inner expander including surface engaging portions interlockable with inner surface engaging portions in the outer expandable members. A device can include the inner expander having an outwardly flared proximal portion that can interlock with the proximal end of the outer expandable members. A device can include a locking bridge expandable with an expandable body, such as an inflatable balloon, and movable to a locked expanded configuration. A bone fusion system, a bone fusion device kit, and/or a method for fusing bone can include such a bone fusion device.

25 Claims, 19 Drawing Sheets

U.S. PATENT DOCUMENTS

| | | |
|---|---|---|
| 6,764,515 B2 | 7/2004 | Ralph |
| 6,773,460 B2 | 8/2004 | Jackson |
| 6,814,734 B2 | 11/2004 | Chappuis |
| 6,821,298 B1 | 11/2004 | Jackson |
| 6,835,206 B2 | 12/2004 | Jackson |
| 6,893,464 B2 | 5/2005 | Kiester |
| 6,918,934 B2 | 7/2005 | Ralph |
| 6,955,691 B2 | 10/2005 | Chae |
| 7,011,658 B2 | 3/2006 | Young |
| 7,018,415 B1 | 3/2006 | McKay |
| 7,056,321 B2 | 6/2006 | Pagliuca |
| 7,087,055 B2 | 8/2006 | Lim |
| 7,118,598 B2 | 10/2006 | Michelson |
| 7,128,760 B2 | 10/2006 | Michelson |
| 7,141,070 B2 | 11/2006 | Ralph |
| 7,153,281 B2 | 12/2006 | Holmes |
| 7,179,225 B2 | 2/2007 | Shluzas |
| 7,217,293 B2 | 5/2007 | Branch, Jr. |
| 7,226,451 B2 | 6/2007 | Shluzas |
| 7,226,482 B2 | 6/2007 | Messerli |
| 7,267,690 B2 | 9/2007 | Felt |
| 7,285,135 B2 | 10/2007 | McKay |
| 7,291,152 B2 | 11/2007 | Abdou |
| 7,303,584 B2 | 12/2007 | Castro |
| 2002/0143401 A1* | 10/2002 | Michelson ............. 623/17.16 |
| 2004/0215191 A1* | 10/2004 | Kitchen ..................... 606/61 |
| 2005/0143825 A1* | 6/2005 | Enayati .................. 623/17.16 |
| 2006/0212118 A1 | 9/2006 | Abernathie |
| 2006/0253201 A1* | 11/2006 | McLuen ................. 623/17.15 |
| 2007/0118171 A1 | 5/2007 | Reiley |
| 2007/0219634 A1* | 9/2007 | Greenhalgh et al. ....... 623/17.16 |
| 2008/0243255 A1* | 10/2008 | Butler et al. ............... 623/17.16 |

FOREIGN PATENT DOCUMENTS

| | | |
|---|---|---|
| WO | 02071921 A2 | 9/2002 |
| WO | 2006051547 A2 | 5/2006 |
| WO | 2006127848 A2 | 11/2006 |
| WO | 2006127849 A2 | 11/2006 |
| WO | WO 2007/022021 A1 | 2/2007 |

* cited by examiner

BONE FUSION DEVICE AND METHODS

FIELD OF THE INVENTION

The present invention relates to bone fusion devices, systems, kits, and methods. Embodiments of the present invention can be used for fusion of joints, and may be particularly useful for fusion of intervertebral joints.

BACKGROUND

Spinal fusion, also known as spondylosyndesis, is a surgical procedure in which two or more vertebrae are fused together to stop the motion between them. Spinal fusion can be used to treat various pathological and/or traumatic conditions, including, for example: injury to the vertebrae; protrusion and/or degeneration of the intervertebral disc between vertebrae ("slipped" disc or herniated disc); abnormal curvatures of the spine (such as scoliosis or kyphosis); and a weak or unstable spine caused by infections or tumors. Spinal fusion can eliminate motion between vertebral segments, which can be a significant source of pain in some patients. The surgery can also stops the progress of spinal deformity, such as scoliosis.

Some approaches to spinal fusion include implanting a bone fusion device, or interbody cage, in the intervertebral space between adjacent vertebrae. Bone fusion devices can be used to distract adjacent vertebrae away from each other, or expand a collapsed disc space between two vertebrae. Restoring height to collapsed disc spaces can relieve painful pressure on nerves. Such devices can stabilize the vertebrae by preventing them from moving relative to each other while fusion occurs. Bone fusion devices can provide a space for inserting bone growth promotion material such as bone grafts and other bone growth promoting agents between adjacent vertebrae. Over time, the vertebrae and bone graft can grow together through and/or around the device so as to fuse the vertebrae.

Conventional bone fusion devices can have various configurations and may be implanted and/or operated in a variety of ways. For example, conventional bone fusion cages can be cylindrical, rectangular, elliptical, tapered, or other shapes. Such conventional devices may be hollow and can include openings through which bone growth promotion material can contact adjacent bone. Insertion of a bone fusion implant may be accomplished through an open surgical procedure through a relatively large incision. Alternatively, a bone fusion implant may be inserted using a minimally invasive surgical procedure, for example, through percutaneous insertion. Certain conventional bone fusion devices include external threads so that the device can be threaded into adjacent vertebrae having been drilled and tapped for that purpose.

Some conventional bone fusion devices comprise cylindrical cages having a width substantially equivalent to the height of the cage. Although larger heights may be clinically indicated, wider implants are generally not desirable since increased width requires removal of more bone for access to the intervertebral space, which can lead to decreased stability, and more retraction of nerve roots, which can lead to temporary or permanent nerve damage.

Other conventional bone fusion devices include vertebral support components (for example, plates) that are movable from a collapsed state to an expanded state. Such support plates may allow the width of the device to be varied so as to accommodate vertebrae of various sizes. These devices have disadvantages. For example, the support plates may require expansion prior to insertion, or the plates may be operatively connected by externally disposed linkage mechanisms, either of which can cause the device to have dimensions requiring an undesirably large incision for (minimally invasive) delivery to an intervertebral space. Other devices may be expandable after being inserted, but can be difficult to operate in a restricted space such as a collapsed intervertebral space.

Conventional bone fusion devices can involve other difficulties or be associated with other less desirable results. For example, some conventional fusion devices are designed to be impacted into the intervertebral space, which can lead to difficulty in placing the device in a desired position, and can unnecessarily traumatize the vertebral bodies or surrounding nerve and/or vascular tissue. Some of the interbody fusion devices rely on gravity alone to stabilize the device between vertebrae, which can lead to undesirable motion between the vertebrae and difficulty in achieving a complete fusion, at least without the aid of some additional stabilizing device, such as a rod or plate. Moreover, some of the devices are not structurally strong enough to support the heavy loads and bending forces at certain levels of the spine, in particular, the lumbar spine. The designs of some of bone fusion cages allow "stress-shielding" of the bone within the cage. Since bone growth is enhanced by stressing or loading the bone material, such "stress-shielding" can greatly increase the time for complete bone growth, or disturb the quality and density of the ultimately formed fusion mass.

Thus, what is desired is a bone fusion device that can be inserted in a minimally invasive manner, that is easily deployed, that provides strong and stable support between adjacent vertebrae, and that promotes optimal bone growth and spinal fusion.

SUMMARY OF THE INVENTION

Some embodiments of the present invention can include a bone fusion device having a plurality of elongated interlockable segments, each segment having at least a first side and a second side, each along a longitudinal axis of the segment. The bone fusion device can further include a first engaging surface along the first side, and a second mateably engaging surface along the second side. A first one of the segments can be inserted into a location between bones. The first engaging surface on the first segment can be slidably engaged with the second engaging surface on a second one of the segments inserted into the location, so that the first and second segments are lockable together side by side in the location. In certain embodiments, the first engaging surface can further comprise a channel, and the second engaging surface can further comprise a rib interlockable with the channel. In some embodiments, the longitudinal axis of the segments of the bone fusion device can be oriented perpendicularly to a vertical axis of a spinal column.

In some embodiments, the device can further include a delivery tube detachably attachable to a proximal end of each of the segments. The delivery tube can comprise a size slightly larger than an outer dimension of a single segment such that the device can be delivered to the location utilizing a minimally invasive procedure. In some embodiments, the device can further include a guide wire insertable through the delivery tube and through a longitudinal lumen in the segment. The guide wire can be adapted control a position of the first segment while the second segment is locked to the first segment.

The present invention can include embodiments of a bone fusion system, a bone fusion device kit, and/or a method for fusing bone, including providing a bone fusion device comprising a plurality of interlockable segments and a delivery tube. The method can further include attaching a delivery tube to a proximal end of a first one of the segments; positioning the first segment with the delivery tube in a location between bones; detaching the delivery tube from the first segment; attaching the delivery tube to a proximal end of a second one of the segments; positioning the second segment with the delivery tube in the location adjacent the first segment; interlocking the first and second segments in the location; and detaching the delivery tube from the second segment. The method can further include using a guide wire to control a position of the first segment while the second segment is locked to the first segment.

Some embodiments of the present invention can include a bone fusion device including an outer expandable component having a plurality of outer expandable members insertable to a location between bones in an unexpanded configuration. The device can further include an inner expander movable from a proximal end toward a distal end of the outer expandable component to expand the outer expandable members into an expanded configuration. The device can further include inner surface engaging portions in the outer expandable members and outer surface engaging portions on the inner expander matingly engageable and interlockable with the inner surface engaging portions in the outer expandable members in the expanded configuration.

In certain embodiments, the inner expander can further include an outside dimension larger than an inside dimension of the outer expandable component. In some embodiments, the outer expandable members can be completely separable from each other. In some embodiments, the outer expandable members can be uniformly expanded by the inner expander along the longitudinal axis of the outer expandable members. In particular embodiments, the bone fusion device can further include an inner rod detachably attached to the outer expandable component and a pushing tube detachably attached to the inner expander. The inner expander and the attached pushing tube can slide about the inner rod so that a distal end of the inner expander can engage the outer expandable component. In certain embodiments, the outer surface engaging portions can further include a plurality of locking flanges extending outwardly from the outer surface of the inner expander. The inner surface engaging portions in each of the outer expandable members can further include a locking channel configured to matingly interlock with one of the locking flanges.

The present invention can include embodiments of a bone fusion system, a bone fusion device kit, and/or a method for fusing bone, including providing a bone fusion device comprising a bone fusion device comprising an outer expandable component having a plurality of outer expandable members, each outer expandable member having an inner surface engaging portion. The outer expandable component can be inserted to a location between bones in an unexpanded configuration. The inner expander having outer surface engaging portions matingly engageable with the inner surface engaging portions can be moved from a proximal end toward a distal end of the outer expandable component to expand the outer expandable members into an expanded configuration. In this way, each of the outer surface engaging portions can be locked together with one of the inner surface engaging portions to lock the inner expander together with the outer expander members. In certain embodiments, the outer expandable members can be expanded into complete separation from each other.

Some embodiments of the present invention can include a bone fusion device having an outer expandable component having a plurality of outer expandable members insertable to a location between bones in an unexpanded configuration. The bone fusion device can further include an inner expander movable from a proximal end toward a distal end of the outer expandable component to expand the outer expandable members into an expanded configuration. The inner expander can further include an outwardly flared proximal portion that can be interlockable with a proximal end of the outer expandable members such that the inner expander remains locked together with the expanded outer expanding members in the expanded configuration.

The present invention can include embodiments of a bone fusion system, a bone fusion device kit, and/or a method for fusing bone, including a bone fusion device comprising a bone fusion device comprising an outer expandable component having a plurality of outer expandable members, and an inner expander having an outwardly flared proximal portion that can be interlockable with a proximal end of the outer expandable members.

Some embodiments of the present invention can include a bone fusion device having an outer expandable component comprising a plurality of outer expandable members. Each outer expandable member can cooperate in an unexpanded configuration to define a lumen, and can have at least one separable interface with another one of the outer expandable members along a length of the device. The device can further include a locking bridge at each interface connecting each outer expandable member with another one of the outer expandable members. The locking bridge can be movable from the unexpanded configuration to a locked expanded configuration. The device can further include an expandable body, such as an inflatable balloon, insertable into the lumen of the outer expandable component and adapted to expand the outer expandable members into the expanded configuration. When the outer expandable members are expanded by the expandable body into the expanded configuration, each locking bridge can lock the expandable members together.

The present invention can include embodiments of a bone fusion system, a bone fusion device kit, and/or a method for fusing bone, including bone fusion device having an outer expandable component comprising a plurality of outer expandable members. The method can further include inserting the device between adjacent bones utilizing a minimally invasive surgical procedure; expanding the expandable members with an expandable body; and locking the expandable members in an expanded configuration with a locking bridge.

Features of a device, system, kit, and/or method of the present invention may be accomplished singularly, or in combination, in one or more of the embodiments of the present invention. As will be realized by those of skill in the art, many different embodiments of a device, system, kit, and/or method according to the present invention are possible. Additional uses, advantages, and features of the invention are set forth in the illustrative embodiments discussed in the detailed description herein and will become more apparent to those skilled in the art upon examination of the following.

DETAILED DESCRIPTION

Figure 1:
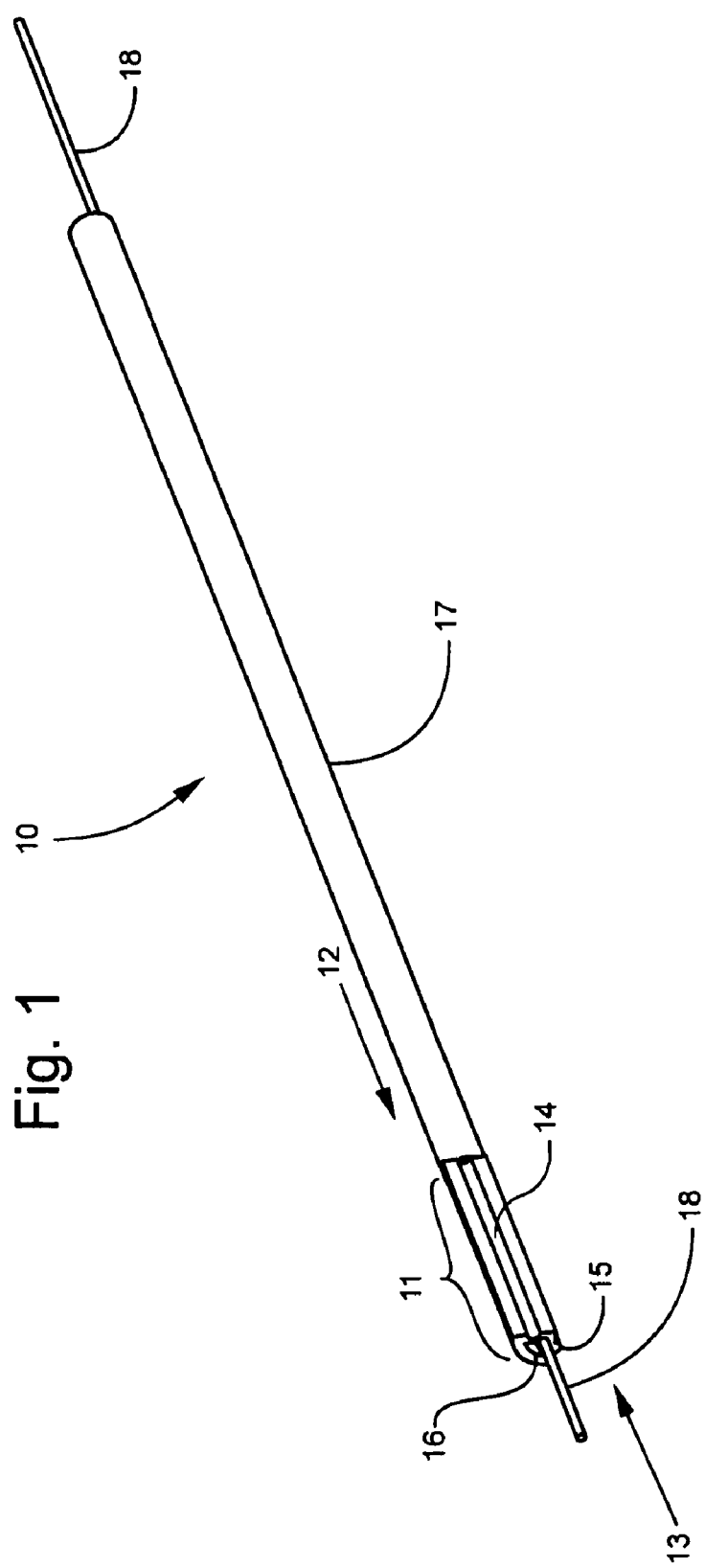
FIG. 1 is a perspective view of a bone fusion device having one of a plurality of interlocking segments, a delivery tube, and a guide wire in an embodiment of the present invention.
Figure 2:
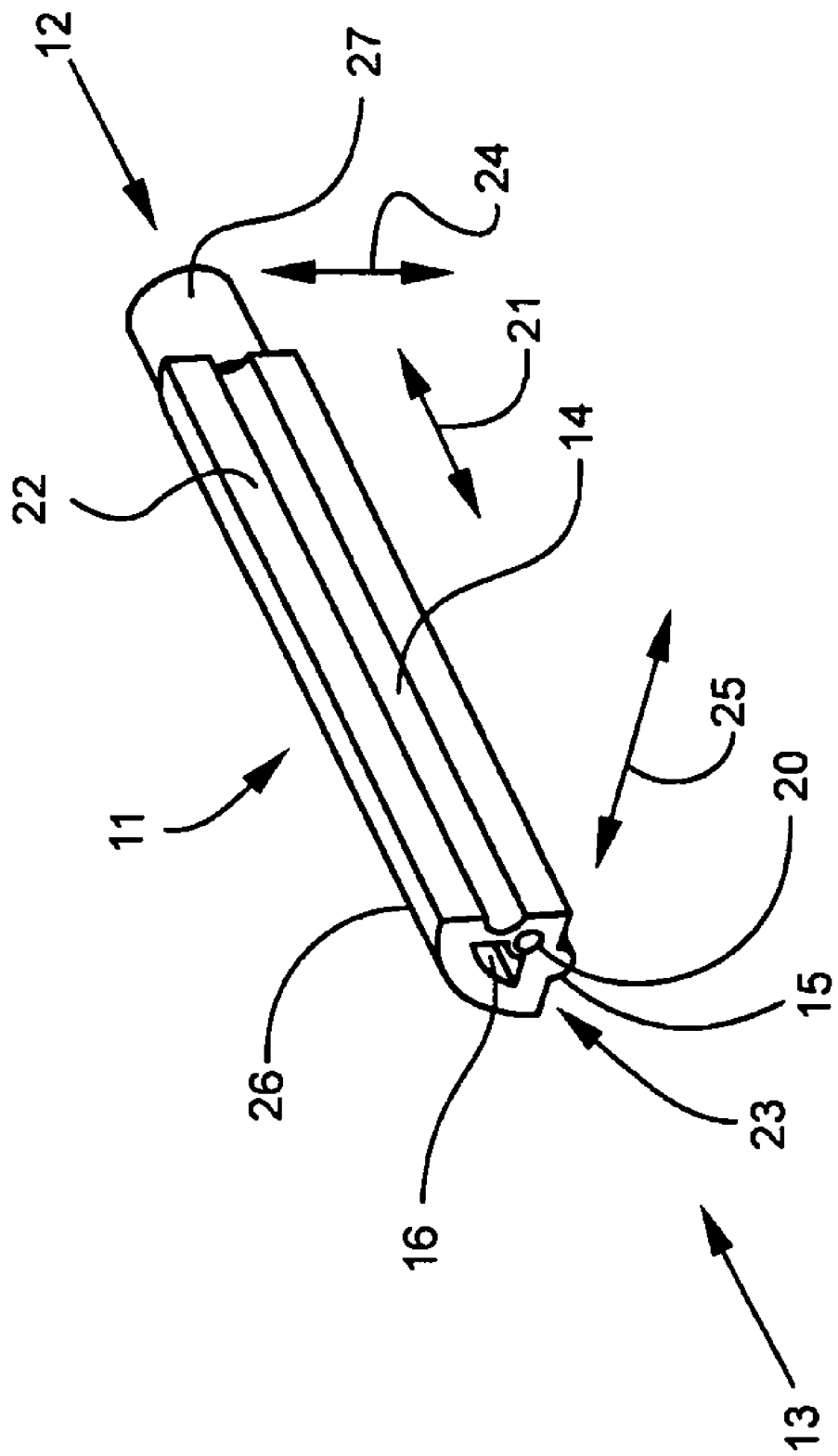
FIG. 2 is a perspective view of the interlocking segment shown in FIG. 1 in an embodiment of the present invention.

For the purposes of this specification, unless otherwise indicated, all numbers expressing quantities, conditions, and so forth used in the specification are to be understood as being modified in all instances by the term "about." Accordingly, unless indicated to the contrary, the numerical parameters set forth in the following specification are approximations that can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, for example, 5.5 to 10. Additionally, any reference referred to as being "incorporated herein" is to be understood as being incorporated in its entirety.

As used in this specification and the appended claims, the singular forms "a," "an," and "the" include plural referents unless the context clearly dictates otherwise. Thus, for example, the term "a projection" is intended to mean a single projection or a combination of projections. As used in this specification and the appended claims, "proximal" is defined as nearer to a point of reference such as an origin, a point of attachment, or the midline of the body. As used in this specification and the appended claims, "distal" is defined as farther from a point of reference, such as an origin, a point of attachment, or the midline of the body. Thus, the words "proximal" and "distal" refer to direction nearer to and farther from, respectively, an operator (for example, surgeon, physician, nurse, technician, etc.) who inserts a medical device into a patient, with the tip-end (i.e., distal end) of the device inserted inside the patient's body. For example, the end of a medical device inserted inside the patient's body is the distal end of the medical device, while the end of the medical device outside the patient's body is the proximal end of the medical device.

As used herein, a "desired" disc space, or "desired" disc space height, refers to the distance between two vertebrae which is determined to be appropriate for the particular condition of the patient. Thus, depending on the condition, the desired height may be that of the normal disc space when in a non-diseased condition, or the disc space may be greater than the normal disc space height or less than normal.

In one aspect of the present invention, some embodiments of the bone fusion device 10 can comprise a plurality of interlockable segments 11 that can be delivered one at a time to a location between bones and assembled in situ, that is, in place at the surgical site. The target location for placement of the device can be, for example, in the intervertebral space 97 between adjacent vertebral bodies 96. The bone fusion device 10 can be delivered to the surgical site utilizing a minimally invasive procedure.

Embodiments of the bone fusion device 10 can include various numbers of interlockable segments 11, for example, two or more segments 11. Each segment 11 can include an interlocking mechanism that allows the assembled bone fusion device 10 to be locked together in a stable manner so as to reduce implant migration during the bone in-growth process. FIGS. 1-4 illustrate embodiments of such a bone fusion device 10 having four interlockable segments 11. In these embodiments, each of the four segments 11 has the shape of one quadrant of a cylinder, such that when the four quadrant segments 11 are inserted to the surgical site and assembled side-by-side, the final bone fusion device implant design is that of a cylinder.

Figure 20:
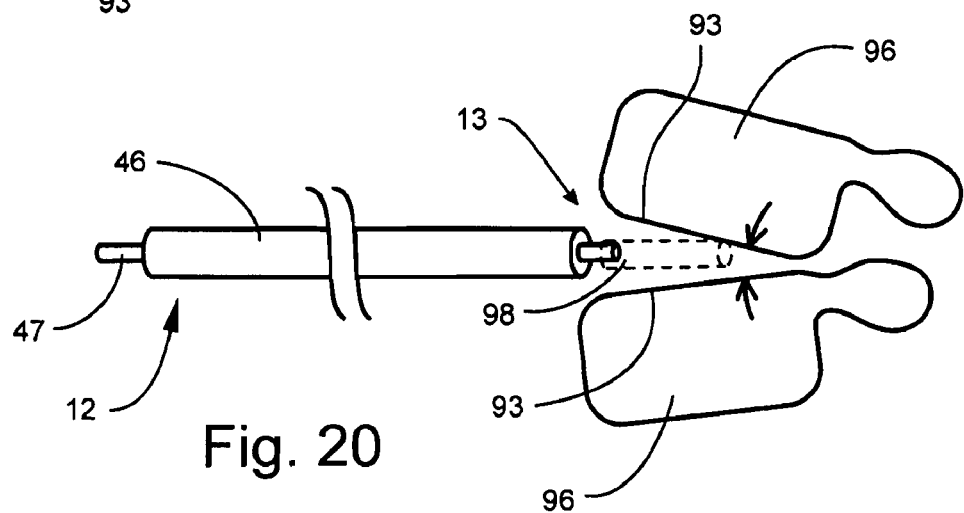
FIG. 20 is a diagrammatic side view of two vertebral bodies with the intervertebral disc removed and showing the inner rod and pushing tube in position to deliver the bone fusion device into the intervertebral space between the two vertebral bodies. The bone fusion device is not shown, but its position is represented in phantom lines.
Figure 21:
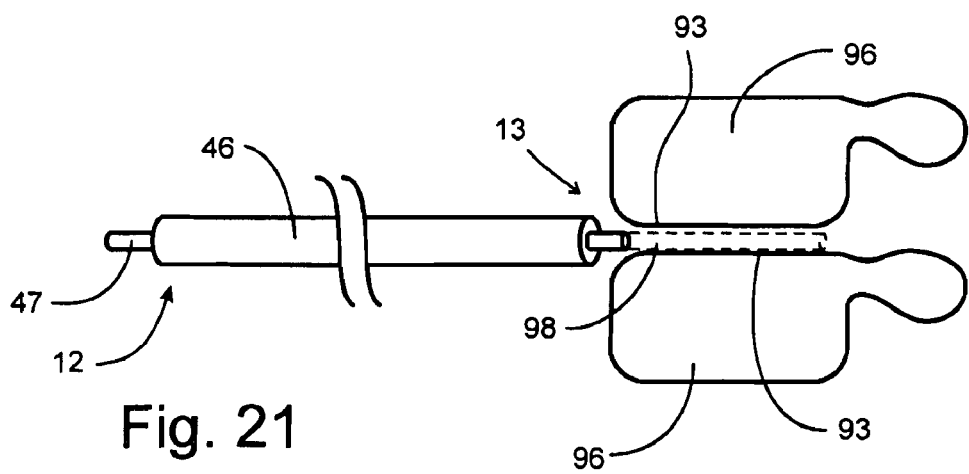
FIG. 21 is a diagrammatic side view of two vertebral bodies with the intervertebral disc removed and showing the inner rod and pushing tube in position after delivery of the bone fusion device into the intervertebral space between the two vertebral bodies. The bone fusion device is not shown, but its position is represented in phantom lines. The two vertebral bodies are separated to a desired intervertebral space height therebetween.

In some embodiments, as shown in FIGS. 1-4, each interlocking segment 11 can comprise an elongated portion of material having a proximal end 12 and a distal end 13. As one quadrant of a cylinder, the segment 11 can have a first side 22 along a first transverse axis 24 and a second side 23 along a second transverse axis 25 perpendicular to the first side 22 and axis 24. The cylinder quadrant-shaped segment 11 can include a third side forming a rounded, outer cylinder surface 26 between the first and second sides 23, 23, respectively. In some embodiments, the interlockable features can include an interlocking channel 14 along the longitudinal axis 21 of the segment 11 in the first transverse side 22. The interlockable features can further include an interlocking rib 15 along the longitudinal axis 21 extending outwardly from the second transverse side 23. When the segments 11 are inserted between adjacent vertebral bodies 96, for example, the rib 15 on the second side 23 of one segment 11 can be fit into the channel 14 on the first side 22 of an adjacent segment 11. For the embodiments shown in FIGS. 1-4 comprising segments 11 that are quadrants of a cylinder, each of the four segments 11 can be inserted into the intervertebral space 97 in a side-by-side arrangement, and the rib 15 on each of the segments 11 can be fit into the channel 14 of an adjacent segment 11. In some embodiments, the longitudinal axis 21 of the segments 1 can be oriented generally transversely (or perpendicularly) to the vertical axis of the spinal column 90, as shown in FIGS. 20 and 21.

In some embodiments, the segments 11 of the bone fusion device 10 can include a mechanical interface, for example, a flange (not shown), in the first side 22 of one segment 22, which can be dimensioned to mechanically engage a corresponding groove (not shown) disposed in the second side 23 of another segment 11. The segments 11 of the bone fusion device 10 may be designed with other types of mechanically engaging interfaces, for example, interlocking wedges, locking pins, etc., depending upon a particular purpose.

In certain embodiments, the interlockable ribs 15 and channels 14 can be configured and/or treated to provide a strong fit between the segments 11 such that the segments 11 remain in a desired position during the functional life of the bone fusion device 10. For example, the channels 14 can include a groove and the ribs 15 can include a matingly contoured lip that when interlocked can prevent the segments 11 from sliding apart. In such configurations, the segments can be assembled by sliding one segment 11 longitudinally along a previously inserted segment 11 so as to interlock the rib 15 and channel 14.

In some embodiments, the segments of the bone fusion device can be inserted into a location between bones (for example, the intervertebral space 97) with a delivery cannula 17, or tube. As shown in FIGS. 1-4, the delivery tube 17 can be detachably attached to a proximal attachment extension 27 at the proximal end 12 of each segment 11. The delivery tube 17 can be detachably attached to the proximal attachment extension 27 in various ways. For example, the distal end 13 of the delivery tube 17 and the proximal end 12 of each segment 11 can have mating threads (not shown) so that the delivery tube 17 can be detachably attached to the segments 11 one at a time. In another embodiment, the delivery tube 17 can be detachably attached to the proximal end 12 of the segments 11 by a tab extending from either the delivery tube 17 or the segment 11 that snaps into a receptacle in the other component. Such a tab capture can be released for detaching the delivery tube 17 from the segment 11 with a tab release or by twisting the delivery tube 17 to release the tab from the receptacle. The attachment mechanism can allow the delivery tube 17 to be readily detached from the segment 11 once the segment 11 is assembled in the intervertebral space 97. Since each segment 11 can be delivered to the surgical site individually, the delivery tube 17 can be sized to be just slightly larger than the outer dimension of a single segment 11. Such a limited outer dimension for the segments 11 and the delivery tube 17 can facilitate use of minimally invasive procedures to implant the bone fusion device 10.

Figure 3:
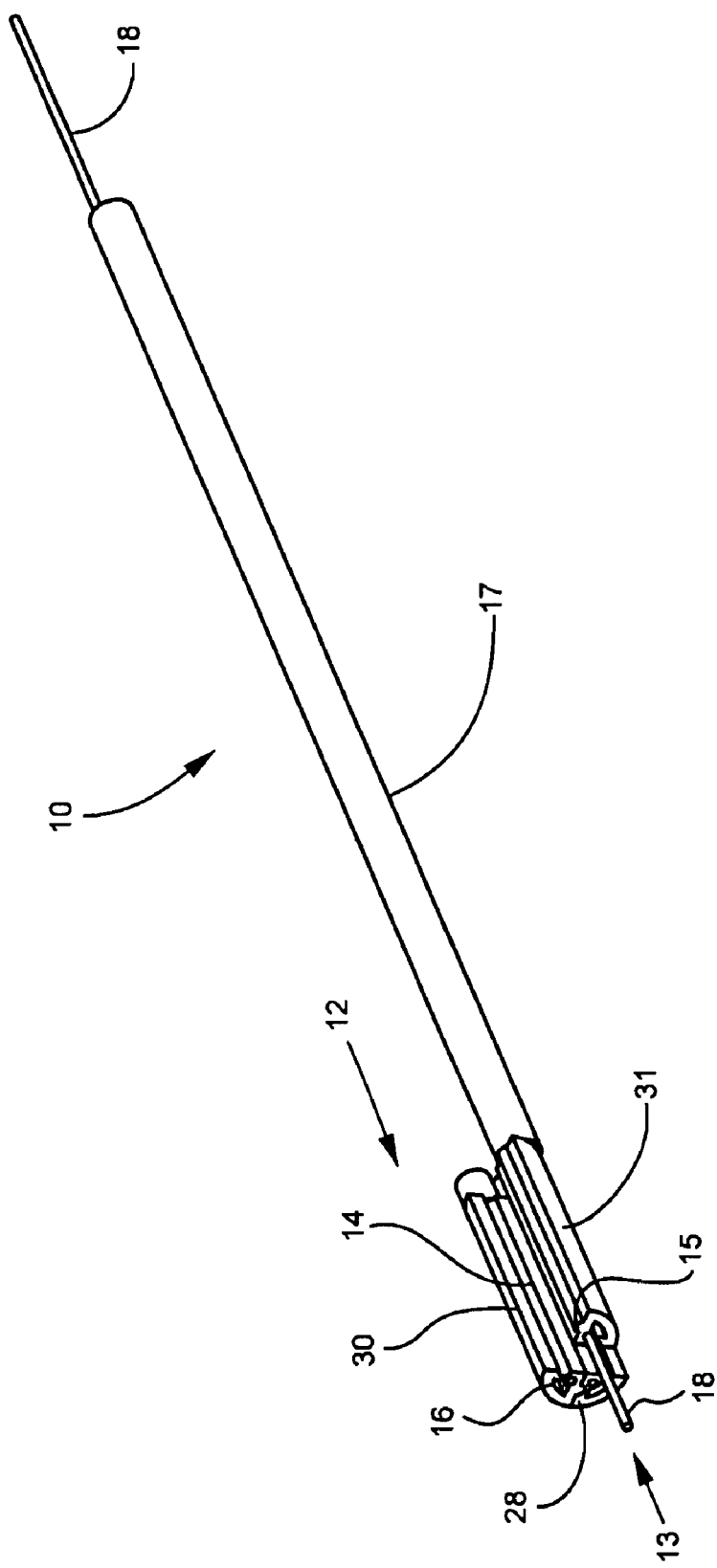
FIG. 3 is a perspective view of the bone fusion device having three of a plurality of interlocking segments partially assembled, a delivery tube, and a guide wire shown in FIG. 1, in an embodiment of the present invention.

As shown in FIGS. 1-4, some embodiments of the bone fusion device 10 can include a longitudinal lumen 20 through each segment 11 through which a guide wire 18, pin, or stylet can be placed for positioning each segment 11 and controlling the segment 11 while another segment 11 is positioned and locked to the other segments 11. The guide wire 18 can be inserted through the delivery tube 17 and through the guide wire lumen 20 in a first segment 28 (as shown in FIG. 3) while the first segment 28 is being positioned in the intervertebral space 97. Once the first segment 28 is in position, the delivery tube 17 can be detached. The guide wire 18, or other insertion guide, can provide control of each segment 11 as adjacent segments 11 are attached. A second segment 30 having another guide wire 18 inserted through its guide wire lumen 20 can then be attached to the distal end 13 of the delivery tube 17 and positioned with the delivery tube 17 adjacent to, and assembled together with, the first segment 28.

As each subsequent segment 11, for example, a third segment 31 and a fourth segment 32, is delivered, it can be positioned adjacent the previously inserted segments 11, and interlocked with the adjacent segments 11. When the final segment 11 is delivered and interlocked with the other implanted segments 11, the delivery tube 17 can be detached and the insertion guide wires 18 removed, leaving the fully assembled bone fusion device 10 implanted between the target bones (for example, the vertebral bodies 96, as shown in FIGS. 20 and 21).

Various components of the bone fusion device 10 can be readjusted throughout the procedure to allow for ease in assembling the device 10 and for accuracy in placing the assembled device 10 in a desired position in the intervertebral space 97. For example, components of the bone fusion device 10 that can be readjusted include segments 11 of the bone fusion device 10 previously positioned in the intervertebral space 97, the delivery cannula 17, and subsequent segments 11 as they are being introduced into alignment and engagement with the previously positioned segments 11.

Embodiments of the bone fusion device 10 can have various sizes, shapes, and overall configurations. For example, the bone fusion device 10 can include four rectangular segments 11 to form a square or rectangular implanted device 10. Similarly, five cylindrical segments 11 can be inserted to create a five-leaf, clover leaf-configured implanted device 10. In other embodiments, the device 10 can comprise round, oval-shaped, kidney-shaped configurations. Various sizes and shapes of the bone fusion device 10 can be selected for use, depending on the desired final dimension and configuration (for example, diameter) for a particular application and patient. For example, differently sized and/or configured bone fusion devices 10 may be preferred for one section of the spinal column 90 and/or for a particular intervertebral disc 94 height and/or anatomy.

In certain embodiments, the bone fusion device 10 can include selected portions that are radiopaque such that delivery and deployment procedures can be visualized under fluoroscopy. In other embodiments, the bone fusion device 10 can be completely radiolucent so that the forming fusion mass in and about the bone fusion device 10 can be visualized radiographically without interference from the device 10.

Figure 4:
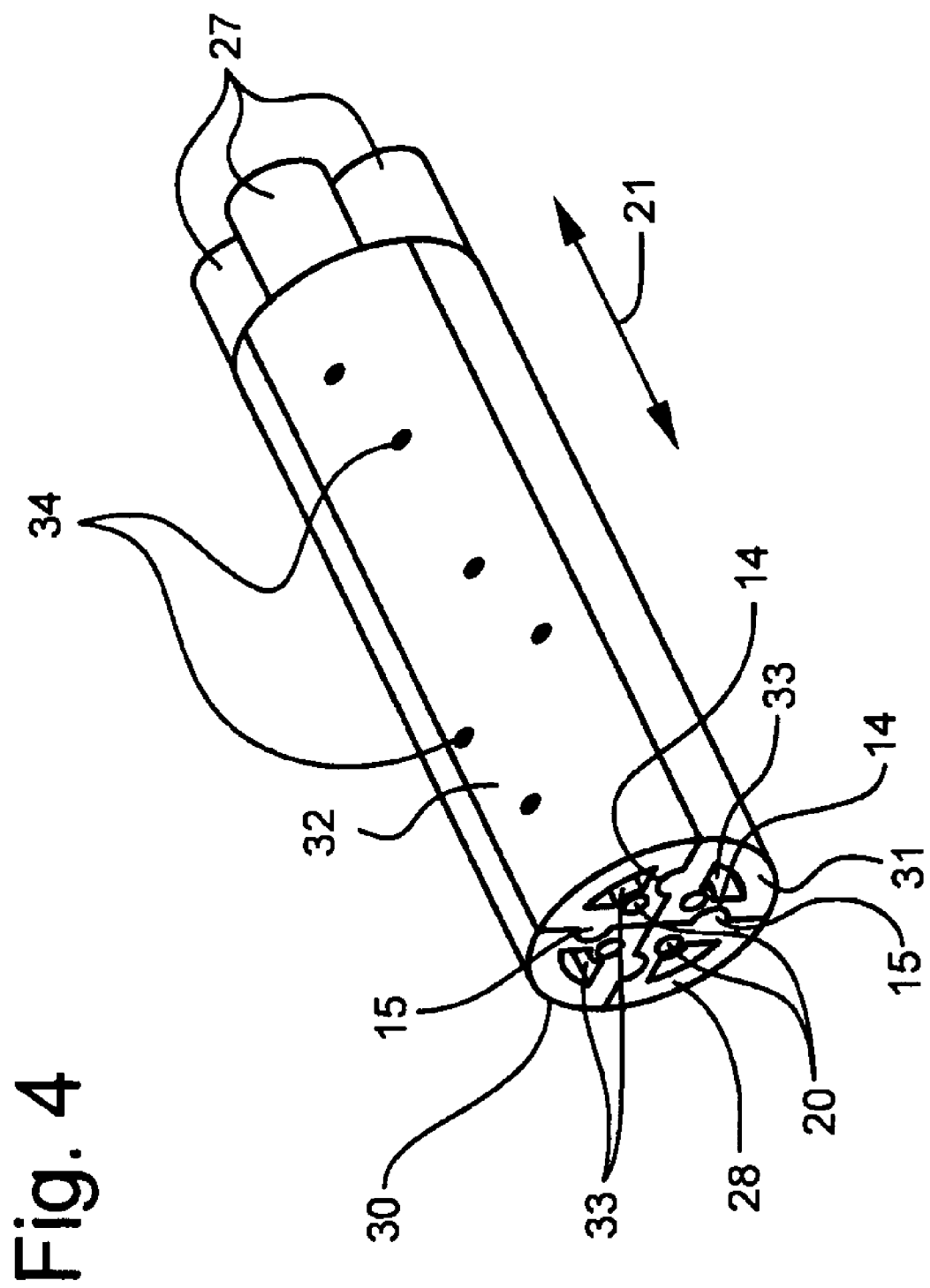
FIG. 4 is a perspective view of the bone fusion device shown in FIG. 3, showing four interlocking segments, fully assembled in an embodiment of the present invention.

In various embodiments of the bone fusion device 10, the outer wall can comprise various surface configurations. Some surface configurations can include bone anchoring elements (not shown) adapted for engagement with adjacent vertebral bodies 96 to prevent or inhibit movement of the bone fusion device 10 once implanted within the intervertebral disc space 97. For example, the outer wall surface can include an arrangement of a plurality of detents. The detents can be arranged in a predetermined fashion (for example, radially) about apertures 34 in the outer wall, for example, as shown in FIG. 4. The detents can be configured so as to project from the outer surface of the outer wall and to engage the adjacent vertebral body 96. The detents can have a spike-like configuration. In such configurations, the detents can serve to anchor the bone fusion device 10 to the adjacent bone structure. The detents may project from the outer surface of the outer wall at varying angles, which may facilitate insertion of the device into the vertebral bodies 96. Other surface configurations adapted to engage the adjacent vertebral bodies 97 include, for example, knurls, ridges, threads, surface roughening, and/or other similar arrangement to facilitate stabilization of the implant 10 in the joint space. In embodiments of the bone fusion device 10 having a circular cross-section, helical threads can be provided for inserting the implant 10 into a tapped or non-tapped disc space 97. In alternative embodiments, the outer surface of the outer wall can have a substantially smooth configuration without any surface projections or irregularities.

The bone fusion device 10 can comprise various suitable biocompatible materials. Such materials may include a polymeric material, including, for example, a non-resorbable polymer such as polyetheretherketone (PEEK) or a resorbable polymer such as polylactates (PLA). Examples of other suitable materials include composite polymers, reinforced polymer composites, carbon fiber, polymethylmethacralate (PMMA), ceramics, and metallic materials such as stainless steel and stainless steel alloys, titanium and titanium alloys, shape-memory alloys, or any combination thereof. In some embodiments, the bone fusion device 10 can comprise materials that provide elasticity similar to that of a bone structure, such as the vertebral body 96. Optimally, some embodiments of the bone fusion device 10 can have sufficient strength to at least partially replace the supporting function of the intervertebral disc 94, that is, to maintain adjacent vertebrae 96 in a desired spaced relation, during healing and fusion. The bone fusion device 10 may be sized and shaped and have adequate strength to be used within the different regions of the vertebra 96, including the cervical, thoracic, and lumbar regions.

In certain embodiments, the bone fusion device 10 can comprise materials that are radiolucent so that a developing fusion mass with the device 10 can be seen under traditional radiographic visualization techniques and in CT scans without enhancement techniques.

In the embodiment shown in FIG. 4, the apertures 34 in the outer wall of the bone fusion device 10 are disposed along substantially the entire length of the device 10. In other embodiments, the apertures, or bone in-growth openings 34, can have different sizes and shapes, and be disposed at different locations and/or in different configurations.

Some embodiments of the bone fusion device 10 can include bone in-growth apertures 34 that support bone growth material in a manner that avoids "stress-shielding," or shielding of the bone growth material, for example, in the interior of the device 10, away from growth-enhancing stresses or loading. For example, in certain embodiments, the bone in-growth apertures 34 can comprise wells in which bone in-growth materials can be placed for immediate contact with the vertebral bodies 96 upon implantation. Certain embodiments can include openings along the ends and sides of the bone fusion device 10 that allow placement of bone in-growth material outside the lumen 33 of the device 10 and into direct contact with the vertebral bodies 96 upon implantation. In this manner, the bone fusion device 10 can retain an optimum amount of bone growth promoting material in contact with adjacent bone.

As an example, in the embodiments shown in FIGS. 1-4, each segment 11 of the bone fusion device 10 can have the longitudinal opening 33 through which bone graft material can be implanted to the surgical site. The longitudinal openings 33 can communicate with transverse openings 34 through the wall (perpendicular to the longitudinal axis 21) in each segment 11. In this way, bone graft material inserted in the longitudinal openings 34 can facilitate contact of the bone growth promoting material with the adjacent bones and enhance in-growth of a bone fusion mass through the fusion device 10 and between the adjacent bones.

In certain embodiments, the guide wire lumen 20 in the segments 11 can communicate with the transverse openings 34 in the walls of the segments 11. In this way, bone growth promoting material can be also be inserted in the guide wire lumen 20, along with insertion into the longitudinal openings 33 for that purpose. As a result, the amount of bone growth promoting material accommodated by the bone fusion device 10 for contacting the adjacent bones can be enhanced.

In some embodiments of the bone fusion device 10, bone growth promoting materials can be loaded or inserted into the interior of the device 10 to facilitate or promote bone growth with and between the adjacent vertebral bodies 96. In some embodiments, the bone growth promoting material can comprise, for example, a bone graft material, such as bone chips or bone marrow, a bone morphogenic protein (BMP), a demineralized bone matrix (DBM), mesenchymal stem cells, a LIM mineralization protein (LMP), and/or any other suitable bone growth promoting material or substance. The bone graft material can be heterologous (xenograft), homologous (allograft), or autologous (autograft) bone, and/or derivatives thereof.

The bone growth promoting material can be loaded into the bone fusion device 10 prior to implantation of the device 10 in the intervertebral space 97. Alternatively, or in addition, the bone growth promoting material can be injected (or packed or loaded) into the bone fusion device 10 after the device 10 is implanted. In embodiments in which the bone fusion device 10 is expanded, the bone growth promoting material can be injected into the bone fusion device 10 before or after the device 10 is expanded. In these manners, immediate contact of the bone growth promoting material with the adjacent bones can be facilitated and fusion of the bones through in-growth of the bone and bone growth promoting material about and through the device 10 between the bones can be enhanced.

Figure 18:
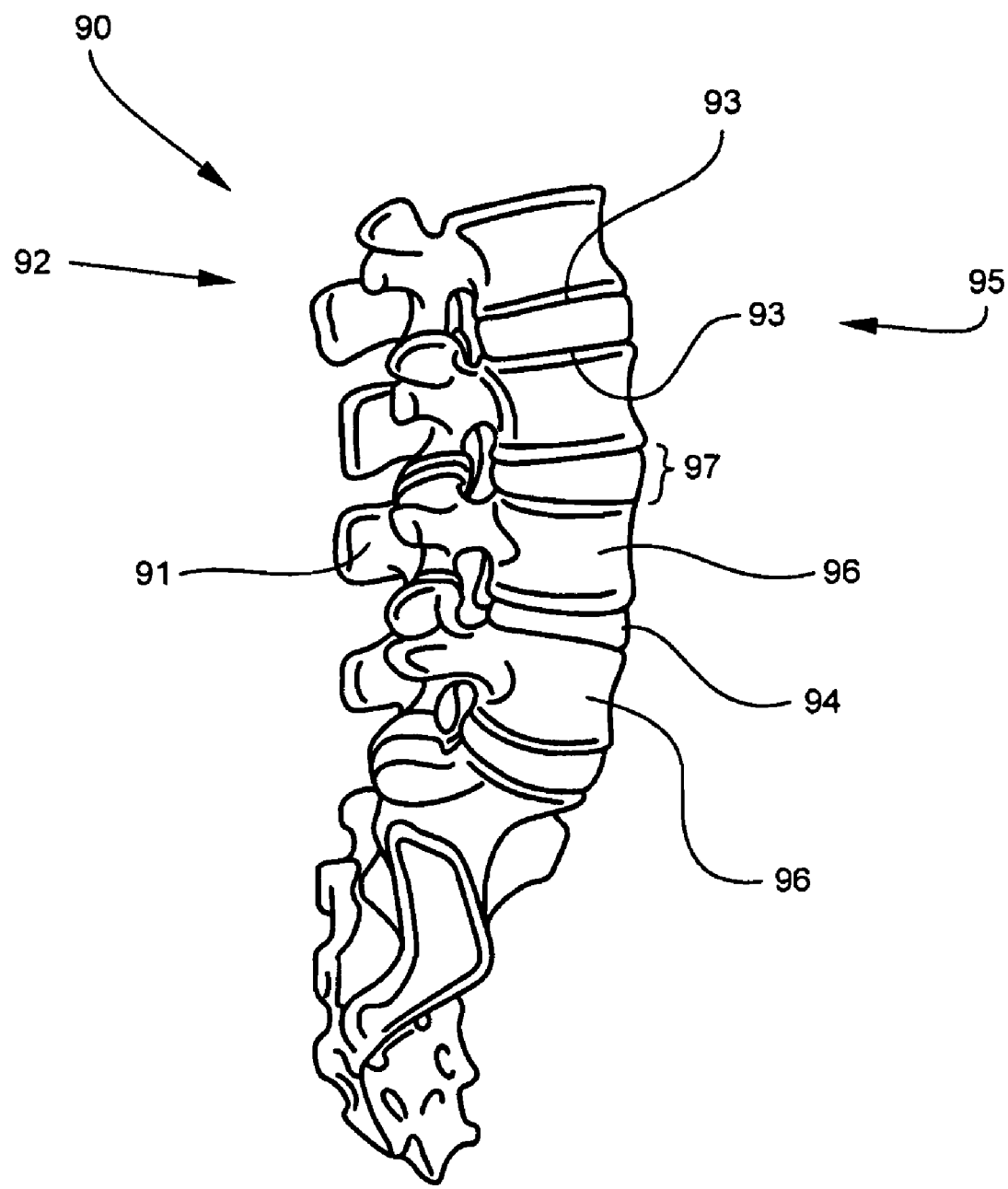
FIG. 18 is a side view of a portion of the anatomy of a spinal column in which some embodiments of the present invention may be useful.

Some embodiments of the bone fusion device 10 of the present invention can be inserted into the intervertebral space 97 in segmented portions 11. Other embodiments can be inserted into the intervertebral space 97 in an unexpanded configuration 51, and then deployed into an expanded configuration 52. FIG. 18 is a side view of a portion of the anatomy of a spinal, or vertebral, column 90. The vertebral column 90 comprises a series of irregularly shaped bones, or vertebral bodies 96. The pedicle 91 is a projection that extends somewhat posteriorly 92 from the vertebral bodies 96. The upper and lower surfaces of each vertebral body 96 include an endplate 93. In between the vertebrae 96 interfacing with the vertebral endplates 93 are intervertebral discs 94 made of fibrous cartilage that act as shock absorbers and allow the back to move. The interveterbral discs 94 are oriented in the anterior 95 direction. As a person ages, these discs 94 can compress and shrink, resulting in a loss of height in the intervertebral disc space 97. Some embodiments of the bone fusion device 10 of the present invention may be useful for restoring intervertebral disc space 97 height after the disc 94 has been removed due to degeneration, disease, or damage, and for promoting bone fusion between adjacent vertebral bodies 96.

Figure 19:
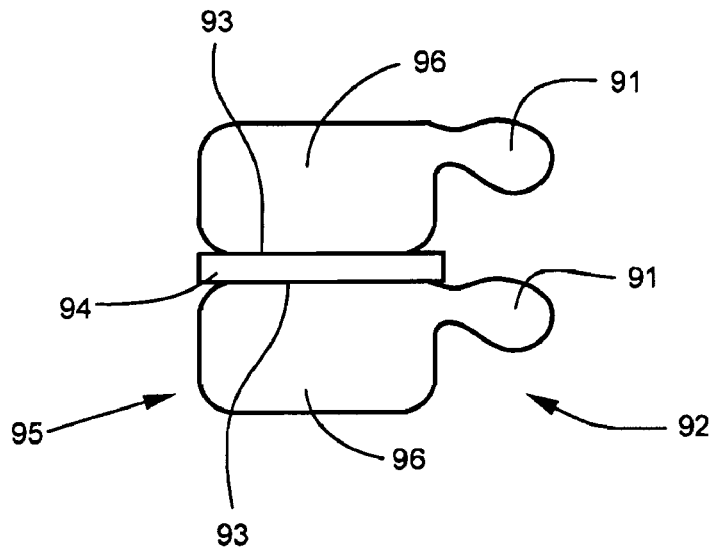
FIG. 19 is a diagrammatic side view of two vertebral bodies with an intervertebral disc in between the vertebral bodies.

FIGS. 19-21 are diagrammatic side views of two vertebral bodies 96. FIG. 19 illustrates the intervertebral disc 94 in between the vertebral bodies 96. In FIGS. 20 and 21, the intervertebral disc 94 has been removed. FIG. 20 depicts the delivery tube 17 and the guide wire 18, or the inner rod 47 and the pushing tube 46, in position to deliver the bone fusion device 10, 40 into the intervertebral space 97 between the two vertebral bodies 96. In FIGS. 20 and 21, the bone fusion device 10 is not shown, but its position 98 is represented in phantom lines. FIG. 21 depicts the delivery tube 17 and the guide wire 18, or the inner rod 47 and pushing tube 46, in position 98 after delivery of the bone fusion device 10 into the intervertebral space 97 between the two vertebral bodies 96. The two vertebral bodies 96 are separated to a desired intervertebral space 97 height between the two vertebral bodies 96.

Various surgical approaches can be utilized to fuse vertebrae 96 using embodiments of the bone fusion device 10. The spine 90 may be approached and the bone fusion device 10 and bone growth promotion material (which may include a bone graft) placed either from the back (posterior 92 approach), from the front (anterior 95 approach), or a combination of both. For example, a posterior lumbar interbody fusion (PLIF) is performed from the back and includes removing the disc 94 between two vertebrae 96 and inserting the bone fusion device 10 and bone growth promoting material into the space 97 created between the two vertebral bodies 96. An anterior lumbar interbody fusion (ALIF) is similar to a PLIF, except that the disc space 97 is fused by approaching the spine 90 through the abdomen instead of through the back. A larger bone fusion device 10 and bone graft may be inserted from an anterior 95 approach. In a PLIF or ALIF procedure, the incisions can be large (for example, 3-6 inches). Alternatively, in an ALIF, the surgeon may use can a minilaparotomy technique with one small incision, or an endoscopic approach through several one-inch incisions. An anterior/posterior 95/92 spinal fusion—from the front and the back—can be utilized for patients with a high degree of spinal instability (for example, fractures). Fusing both the front and back can provide a higher degree of stability for the spine and a large surface area for the bone fusion, which can lead higher fusion rates. Another surgical approach for spinal fusion is the transforaminal lumbar interbody fusion (TLIF) performed from the side. The surgical approach selected for a particular spinal fusion can depend on a number of factors, including, for example, the section of the spine 90 involved, the type of disease, degeneration, or damage to be treated, and overall condition of the patient.

Embodiments of the bone fusion device 10 of the present invention can be inserted utilizing minimally invasive surgical techniques. Open surgical spinal fusion procedures can include a 4-6 inch incision. In contrast, minimally invasive spinal fusion can be performed through a small (for example, two centimeters) incision, or a percutaneous access portal, for access and delivery of instruments and the bone fusion device 10. Such minimally invasive surgery can utilize endoscopic equipment for viewing the surgical site. Due to the smaller access portal to the surgical site, miniaturized instruments, such as scrapers and drills, can be used to operate on the intervertebral space 97. In a minimally invasive procedure, the muscle can be split or moved apart rather than cut, as in an open procedure. As a result, minimally invasive spinal fusion procedures can provide decreased bleeding, less pain, a reduced hospital stay, shorter recuperating time, and less long term tissue damage.

Prior to implanting an embodiment of the bone fusion device 10 of the present invention, the target intervertebral site 97 can be accessed, and at least a portion of the natural intervertebral disc 94 can be removed via a total or partial discectomy. The endplates 93 of the adjacent (upper and lower) vertebrae 96 can then be prepared using surgical instruments and techniques. For example, the endplates 93 of the bone can be scraped, curetted, chiseled, or a similar procedure performed to create an exposed vertebral body end surface for facilitating bone growth across the fusion site. In some clinical circumstances, it may be advantageous to distract the adjacent vertebrae 96 prior to insertion of the bone fusion device 10. Such distraction can provide for easier removal of disc material and/or greater exposure to facilitate preparation of the endplates 93. Distraction can also provide greater accuracy in determining the appropriate size bone fusion device 10 to implant. In some cases, an appropriately-shaped passage between and into the adjacent vertebrae 96 can be formed, for example, by drilling and/or tapping a bore of an approximate size for receiving the bone fusion implant 10. Following preparation of the intervertebral space 97, the bone fusion device 10 can be positioned within the space 97.

In a minimally invasive surgical procedure for inserting an embodiment of the bone fusion device 10, a surgeon may utilize a surgical access device (not shown) comprising an elongate delivery tube, or cannula. Such a surgical access device and minimally invasive technique is further described and shown in co-pending U.S. patent application Ser. No. 11/448,228, which is incorporated herein by reference in its entirety. The surgical access device may include a stylet for percutaneously inserting the delivery cannula 17 to a surgical site. The stylet may include a handle for manipulating the stylet, a pointed tip, and a guide wire bore extending through the length of the stylet. The stylet can be inserted into a lumen of the elongate delivery cannula, and the guide wire bore of the stylet can be guided over a guide wire for positioning the delivery cannula at the surgical site.

The surgical access device may be percutaneously inserted to a targeted intervertebral site using a variety of techniques. In one illustrative embodiment, a stab wound or small incision can be made in a patient's skin above a targeted surgical site. A small insertion cannula (not shown) having a sharp tip, for example, a trocar cannula, can be used to penetrate tissue to the surgical site. A guide wire (not shown) may be inserted through the insertion cannula. The insertion cannula can be removed, leaving the guide wire in place. With the stylet inserted in the lumen of the delivery cannula 17, the stylet and delivery cannula 17 can then be threaded over the guide wire through the central guide wire bore in the stylet. The guide wire can have a diameter and rigidity sufficient to guide the delivery cannula 17 accurately to the surgical site. When the delivery cannula 17 is in a desired position, the guide wire and stylet can be removed from the delivery cannula 17. The bone fusion device 10 attached to the distal end 13 of an inner rod can then be inserted through the lumen of the delivery tube 17 to the intervertebral site 97.

In another illustrative minimally invasive surgical procedure useful with embodiments of the present invention, the insertion cannula utilized to create an initial percutaneous route to the surgical site can be a Jamshidi needle (not shown). The delivery cannula 17 can be threaded over the Jamshidi needle to the surgical site. When the delivery cannula 17 is in a desired position, the Jamshidi needle can be removed from the delivery cannula 17. Alternatively, the insertion cannula and a guide wire, Jamshidi needle, or other insertion mechanism can be placed in the lumen of a stylet and/or delivery cannula 17 and inserted together with the stylet and/or delivery cannula 17 to the surgical site.

Other embodiments of the present invention, for example, the bone fusion devices 40, 60, and 70 can be inserted into a surgical site utilizing the same surgical approaches and procedures as described for the bone fusion device 10.

Some embodiments of the bone fusion device 10 having a plurality of interlocking segments 11 have advantages over conventional bone fusion devices. For example, each segment 11 of the device can be individually inserted into a space between bones. As a result, the bone fusion device 10 can be inserted into the target space utilizing a delivery cannula 17 that is only slightly larger than the outer dimensions of the individual segment 11, thereby allowing insertion using a minimally invasive surgical procedure. Use of a minimally invasive procedure to implant an embodiment of the bone fusion device 10 can help minimize distraction of tissue (such as nerve and vascular tissue) near the surgical site, reduce postoperative pain, and decrease recuperation time. Such a bone fusion device 10 can provide for the alignment, adjustment, and maintenance of the spatial relationship(s) of adjacent bones (for example, 96) during postoperative healing.

The present invention can include embodiments of a bone fusion system and/or a bone fusion device kit. Such a system and/or kit can include embodiments of the bone fusion device 10 as described herein. For example, the bone fusion device 10 can include a plurality of interlockable segments 11 that can be delivered one at a time to a location between bones and assembled in situ.

Each segment 11 can include an interlocking mechanism that allows the assembled bone fusion device 10 to be locked together in a secure and stable manner. The interlocking mechanism can be, for example, the interlocking channel 14 along the longitudinal axis 21 of the segment 11 in the first transverse side 22. The interlocking mechanism can further include the interlocking rib 15 along the longitudinal axis 21 extending outwardly from the second transverse side 23. When the segments 11 are inserted between adjacent vertebral bodies 96, the rib 15 on the second side 23 of one segment 11 can be fit into the channel 14 on the first side 22 of an adjacent segment 11. In some embodiments, the longitudinal axis 21 of the segments 11 can be oriented transversely (or perpendicularly) to the vertical axis of the spine 90.

In some embodiments, a bone fusion system and/or a bone fusion device kit can include the delivery tube 17 by which the segments 11 can be inserted into a location between bones (for example, the intervertebral space 97). The delivery tube 17 can be detachably attached to the proximal end 12 of each segment 11. The attachment mechanism can allow the delivery tube 17 to be readily detached from the segment 11 once the segment 11 is assembled in the intervertebral space 97. Since each segment 11 can be delivered to the surgical site individually, the delivery tube 17 can be sized to be just slightly larger than the outer dimension of a single segment 11. Such a limited outer dimension for the segments 11 and the delivery tube 17 can facilitate use of minimally invasive procedures to implant the bone fusion device 10.

In some embodiments, the bone fusion system and/or a bone fusion device kit can include the guide wire 18 that can be placed through the delivery tube 17 and the longitudinal guide wire lumen 20 in each segment 11 for positioning each segment 11 and controlling the segment 11 while another segment 11 is positioned and locked to the other segments 11. The guide wire 18 can be inserted through the delivery tube 17 and through the guide wire lumen 20 in the first segment 28 (as shown in FIG. 3) while the first segment 28 is being positioned in the intervertebral space 97. Once the first segment 28 is in position, the delivery tube 17 can be detached. The guide wire 18, or other insertion guide, can provide control of each segment 11 as adjacent segments 11 are attached. The second segment 30 having another guide wire 18 inserted through its guide wire lumen 20 can then be attached to the distal end 13 of the delivery tube 17 and positioned with the delivery tube 17 adjacent to, and assembled together with, the first segment 28.

As each subsequent segment 11, for example, the third segment 31 and the fourth segment 32, is delivered, it can be positioned adjacent the previously inserted segments 28, 30, and interlocked with the adjacent segments 28, 30. When the final segment 32 is delivered and interlocked with the other implanted segments 28, 30, 31, the delivery tube 17 can be detached and the insertion guide wires 18 removed, leaving the fully assembled bone fusion device 10 implanted between the target bones (vertebral bodies 96).

The present invention can include embodiments of a method for fusing bone. Such a method can comprise utilizing the bone fusion device 10, system, and/or kit as described herein. For example, one such method can include providing the bone fusion device 10 including a plurality of interlockable segments 11 that can be delivered one at a time to a location between bones and assembled in situ. The method can further include interlocking each segment 11 together in the assembled bone fusion device 10 in a secure and stable manner. The interlocking mechanism can be, for example, the interlocking channel 14 along the longitudinal axis 21 of the segment 11 in the first transverse side 22. The interlocking mechanism can further include the interlocking rib 15 along the longitudinal axis 21 extending outwardly from the second transverse side 23. When the segments 11 are inserted between adjacent vertebral bodies 96, the rib 15 on the second side 23 of one segment 11 can be fit into the channel 14 on the first side 22 of an adjacent segment 11. In some embodiments, the longitudinal axis 21 of the segments 11 can be oriented transversely (or perpendicularly) to the vertical axis of the spine 90.

In some embodiments, the method for fusing bone can further include inserting the segments 11 into a location between bones (for example, the intervertebral space 97) with the delivery tube 17. The delivery tube 17 and the attached segment 11 can be inserted into the intervertebral space 97 through an outer access cannula (not shown). The delivery tube 17 can be detachably attached to the proximal end 12 of each segment 11. The attachment mechanism can allow the delivery tube 17 to be readily detached from the segment 11 once the segment 11 is assembled in the intervertebral space 97. Since each segment 11 can be delivered to the surgical site individually, the delivery tube 17 can be sized to be just slightly larger than the outer dimension of a single segment 11. Such a limited outer dimension for the segments 11 and the delivery tube 17 can facilitate use of minimally invasive procedures to implant the bone fusion device 10.

In some embodiments, the method for fusing bone can further include placing the guide wire 18 through the delivery tube 17 and the longitudinal guide wire lumen 20 in each segment 11 and positioning and controlling the segment 11 while another segment 11 is positioned and locked to the other segments 11. The guide wire 18 can be inserted through the delivery tube 17 and through the guide wire lumen 20 in the first segment 28 (as shown in FIG. 3) while the first segment 28 is being positioned in the intervertebral space 97. Once the first segment 28 is in position, the delivery tube 17 can be detached. The guide wire 18, or other insertion guide, can provide control of each segment 11 as adjacent segments 11 are attached. The second segment 30 having another guide wire 18 inserted through its guide wire lumen 20 can then be attached to the distal end 13 of the delivery tube 17 and positioned with the delivery tube 17 adjacent to, and assembled together with, the first segment 28. As each subsequent segment 11 is delivered, it can be positioned adjacent the previously inserted segments 11, and interlocked with the adjacent segments 11. When the final segment 11 is delivered and interlocked with the other implanted segments 11, the delivery tube 17 can be detached and the insertion guide wires 18 removed, leaving the fully assembled bone fusion device 10 implanted between the target bones (vertebral bodies 96).

In certain embodiments, the method can include accessing opposite sides of the target intervertebral space 97 and inserting one of the bone fusion devices 10 in each side of the space 97. A first side of the intervertebral space 97 can be accessed and the segments 11 of a first bone fusion device 10 can be inserted and locked together in the first side. Once the first bone fusion device 10 is implanted, a second side of the intervertebral space 97 can be accessed and the segments 11 of a second bone fusion device 10 can be inserted and locked together in the second side. Alternatively, the first side of the intervertebral space 97 can be accessed and less than all (for example, one) of the segments 11 of the first bone fusion device 10 can be inserted into the first side. While the access cannula (not shown) remains in place in the first side, the second side of the intervertebral space 97 can be accessed and less than all (for example, one) of the segments 11 of the second bone fusion device 10 can be inserted into the second side. Additional segments of each of the first and second bone fusion devices 10 can then be inserted and assembled with previously inserted segments 11 on each respective side of the intervertebral space 97. Additional segments 11 can be inserted and assembled in the two sides in alternating fashion or in any other order the surgeon may prefer depending on the pathology of the intervertebral space 97 and adjacent vertebral bodies 96, as well as other patient-related and/or surgical techniques factors. In certain embodiments of such methods, the first and second bone fusion devices 10 can be positioned in the intervertebral space 97 in adjacent side-by-side relation.

Once in position in the interveterbral space 97, bone growth inducing substances can be inserted into the bone fusion device(s) 10. The bone fusion device(s) 10 can provide structural support between the adjacent vertebral bodies 96 so as to maintain the desired intervertebral dimensions during the fusion process. Over a period of time, the vertebral tissue can communicate through the apertures 34 within the fusion device 10 to form a solid fusion.

In another aspect of the present invention, some embodiments of the bone fusion device 40 can comprise an outer expandable component 41 having a plurality of outer expandable members 42 insertable to a surgical site in the collapsed, or unexpanded, configuration 51. An inner expander 43 can be inserted in the outer expandable component 41 and moved from the proximal end 12 toward the distal end 13 of the outer expandable component 41 to expand the outer expandable members 42 into the expanded configuration 52. The inner expander 43 can include outer surface engaging portions that can interlock with inner surface engaging portions in the outer expandable members 42 such that the inner expander 43 remains locked together with the expanded outer expanding members 42 in the expanded configuration 52. The bone fusion device 10 can be delivered to a surgical site, for example, in the intervertebral space 97 between adjacent vertebral bodies 96, utilizing a minimally invasive procedure.

As shown in the embodiments in FIGS. 5-9, the bone fusion device 40 can include a plurality of cooperating outer expandable members 42 that in the collapsed, unexpanded configuration 51 together comprise a hollow lumen 45 extending along the longitudinal axis 21 of the device 40. In some embodiments, the lumen 45 of the outer expandable members 42 can be sized and configured to receive the inner expander 43 therein. The relationship of the size and configuration of the outer members 42 and the inner expander 43 can be such that movement of the inner expanding member 43 within the lumen 45 of the outer expandable component 41 engages the outer expandable members 42 to expand along the longitudinal axis 21 of the device 40. As a result, axial displacement of the outer expandable members 42 along the longitudinal axis 21 causes the outer members 42 to separate from each other, thereby transitioning the bone fusion device 40 to the expanded configuration 52. In some embodiments, the outer expandable members 42 can separate completely from each other.

In some embodiments, the bone fusion device 40 can further include the inner rod 47 that can be detachably attached to an outer expandable component attachment point 48 on the distal end 13 of the outer expandable component 41. In some embodiments, attachment of the inner rod 47 to the distal end 13 of the outer expandable component 41 can be a threaded attachment. In other embodiments, attachment of the inner rod 47 to the distal end 13 of the outer expandable component 41 can be, for example, keyed engagement, tongue-and-groove engagement, frictional engagement, or any other suitable method of releasable engagement.

In some embodiments, the bone fusion device 40 can further include a pushing tube 46 that can be detachably attached to an inner expander attachment point 50 on the proximal end 12 of the inner expander 43. In some embodiments, attachment of the pushing tube 46 to the inner expander 43 can be an abutting attachment, or engagement. In other embodiments, attachment of the pushing tube 46 to the inner expander 43 can be, for example, threaded engagement, keyed engagement, tongue-and-groove engagement, frictional engagement, or any other suitable method of engagement. The inner expander 43 and the attached pushing tube 46 can be slid over the inner rod 47 so that the distal end 13 of the inner expander 43 can engage the proximal end 12 of the outer expandable component 41. The inner expander 43 can have an outside dimension larger than the inside dimension of the outer expandable component 41. While the outer expandable component 41 can be held in a desired position in, for example, the intervertebral space 97, with the inner rod 47, the pushing tube 46 can be translated forward to push the inner expander 43 inside the outer expandable component 41. In this way, the inner expander 43 can cause the outer expandable members 42 to move outwardly and apart from each other. As the outer expandable members 42 are expanded apart, they can contact the adjacent vertebral body endplates 93, possibly forcing them apart so as to restore the disc space 97 to its normal height.

Figure 5:
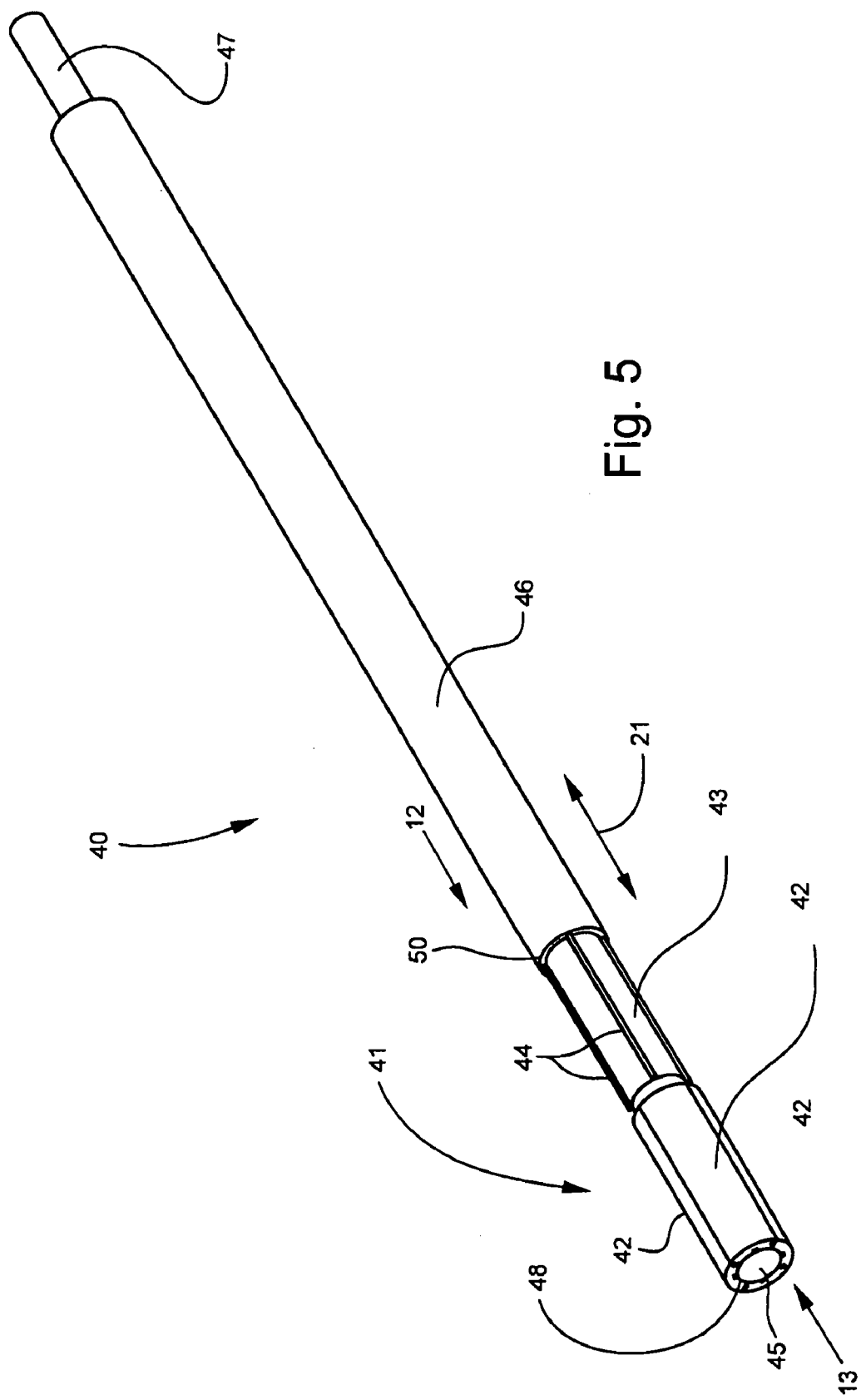
FIG. 5 is a perspective view of a bone fusion device having an outer expandable component comprising a plurality of outer expandable members and an inner expander in an embodiment of the present invention.
Figure 6:
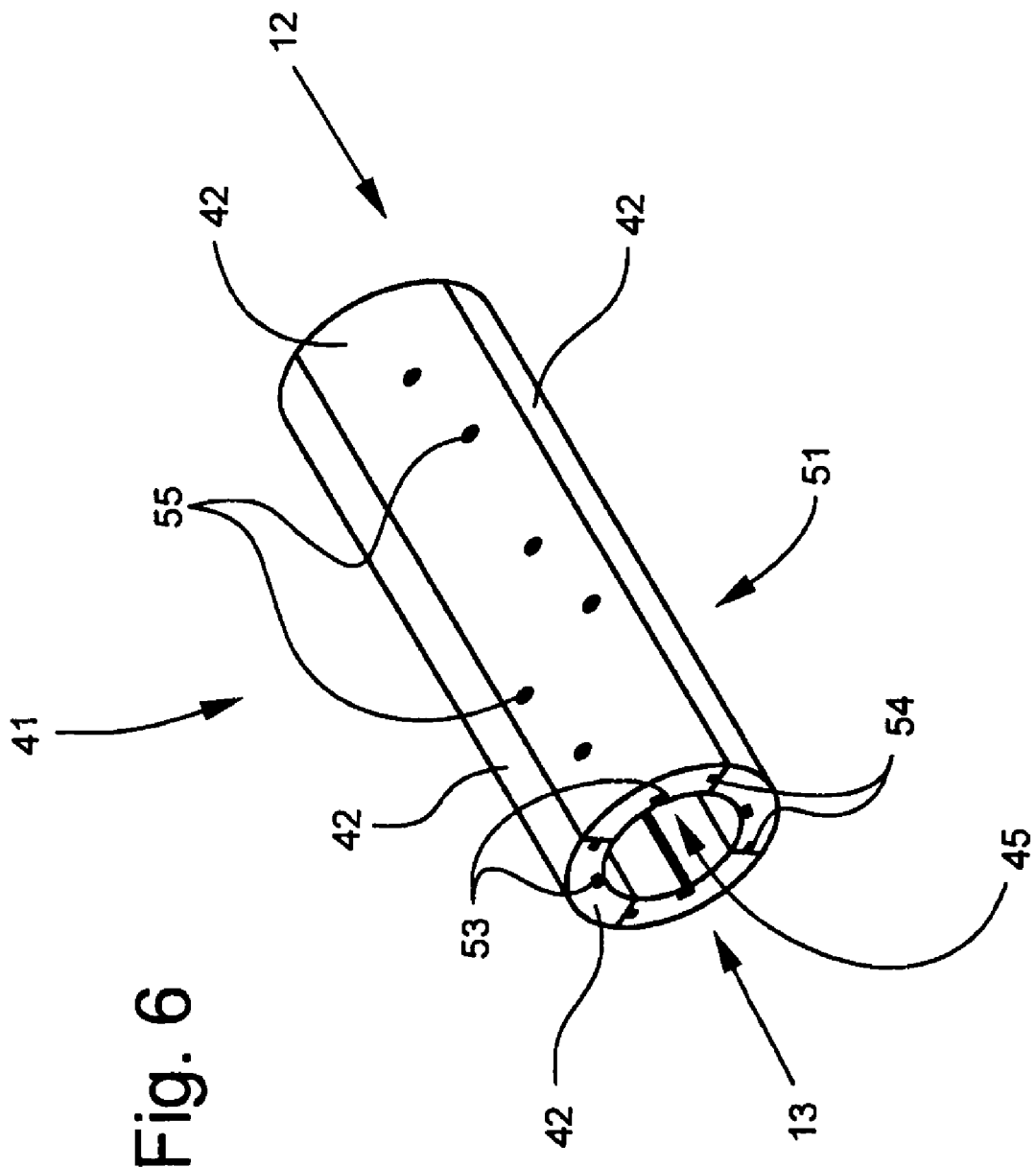
FIG. 6 is a perspective view of the outer expandable component shown in FIG. 5 in the unexpanded configuration in an embodiment of the present invention.
Figure 7:
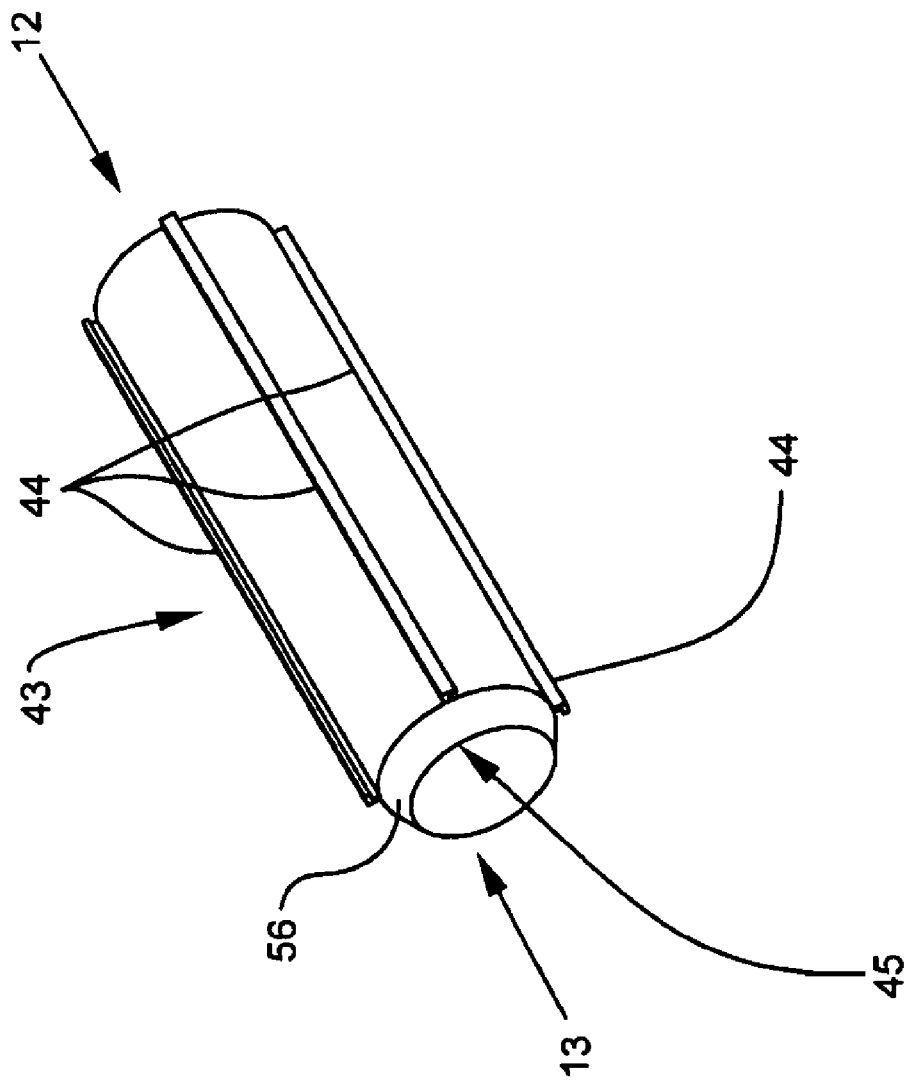
FIG. 7 is a perspective view of the inner expander shown in FIG. 5 in an embodiment of the present invention.
Figure 8:
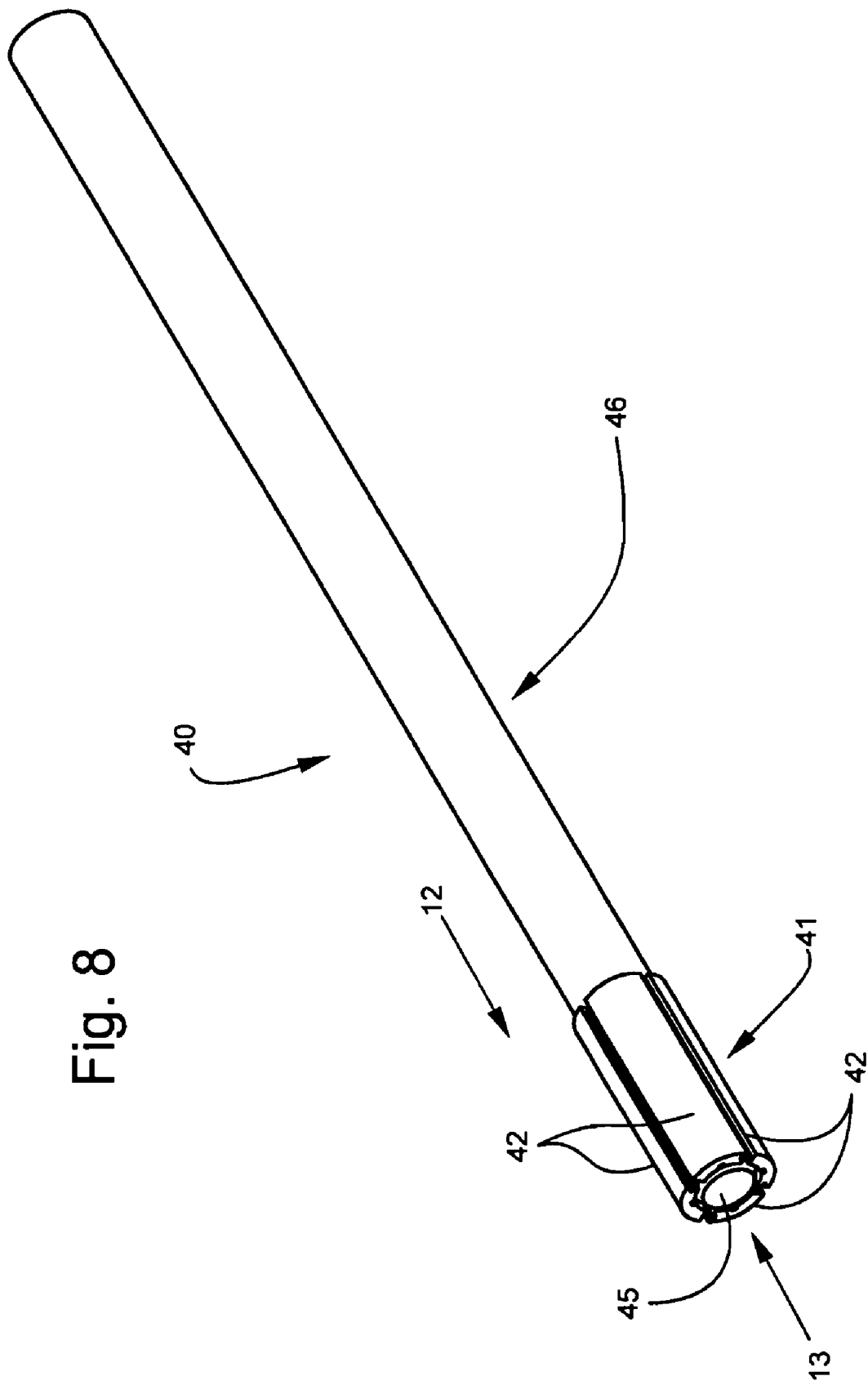
FIG. 8 is a perspective view of the inner expander inserted into the outer expandable component and the outer expandable members in the expanded configuration in an embodiment of the present invention.
Figure 9:
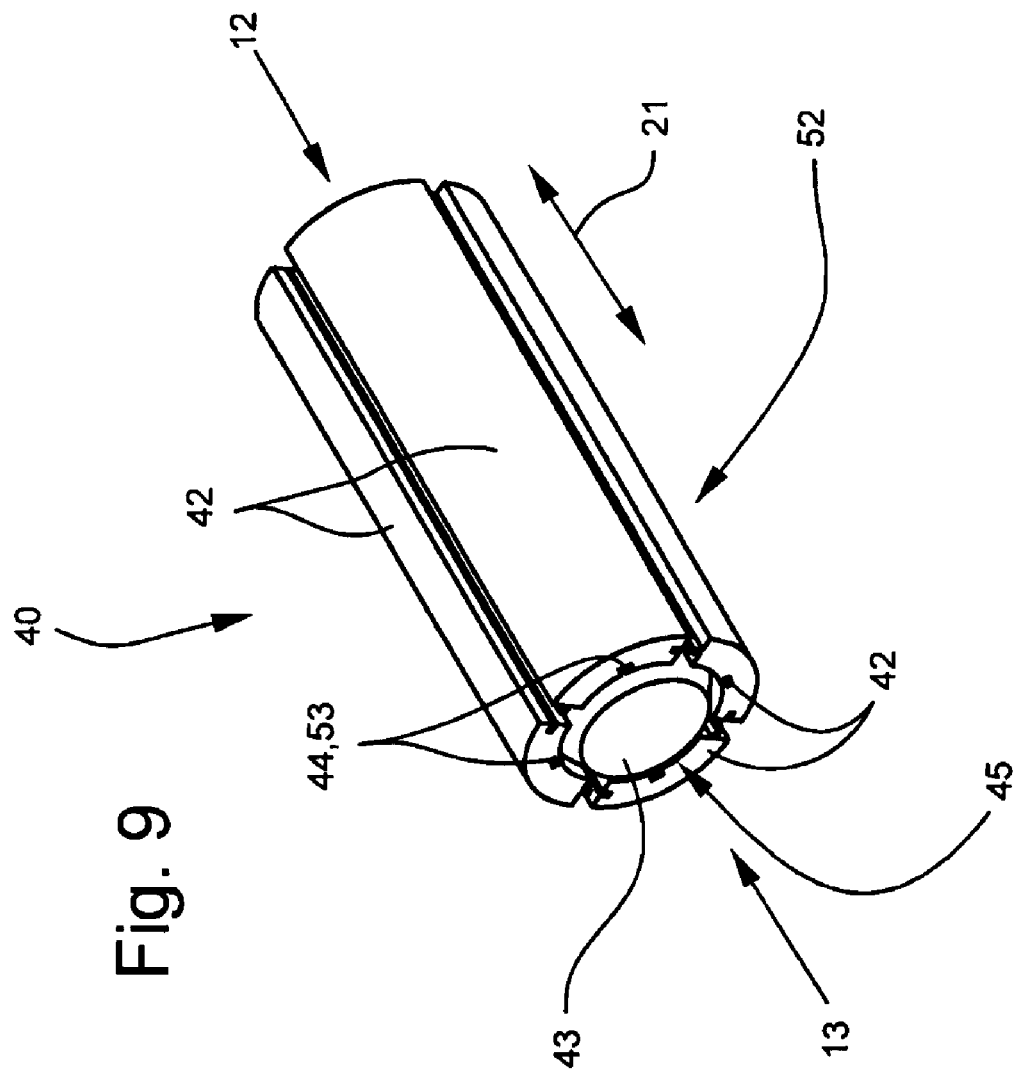
FIG. 9 is a perspective view of the inner expander inserted into and locked together with the outer expandable members in the expanded configuration in an embodiment of the present invention.
Figure 10:
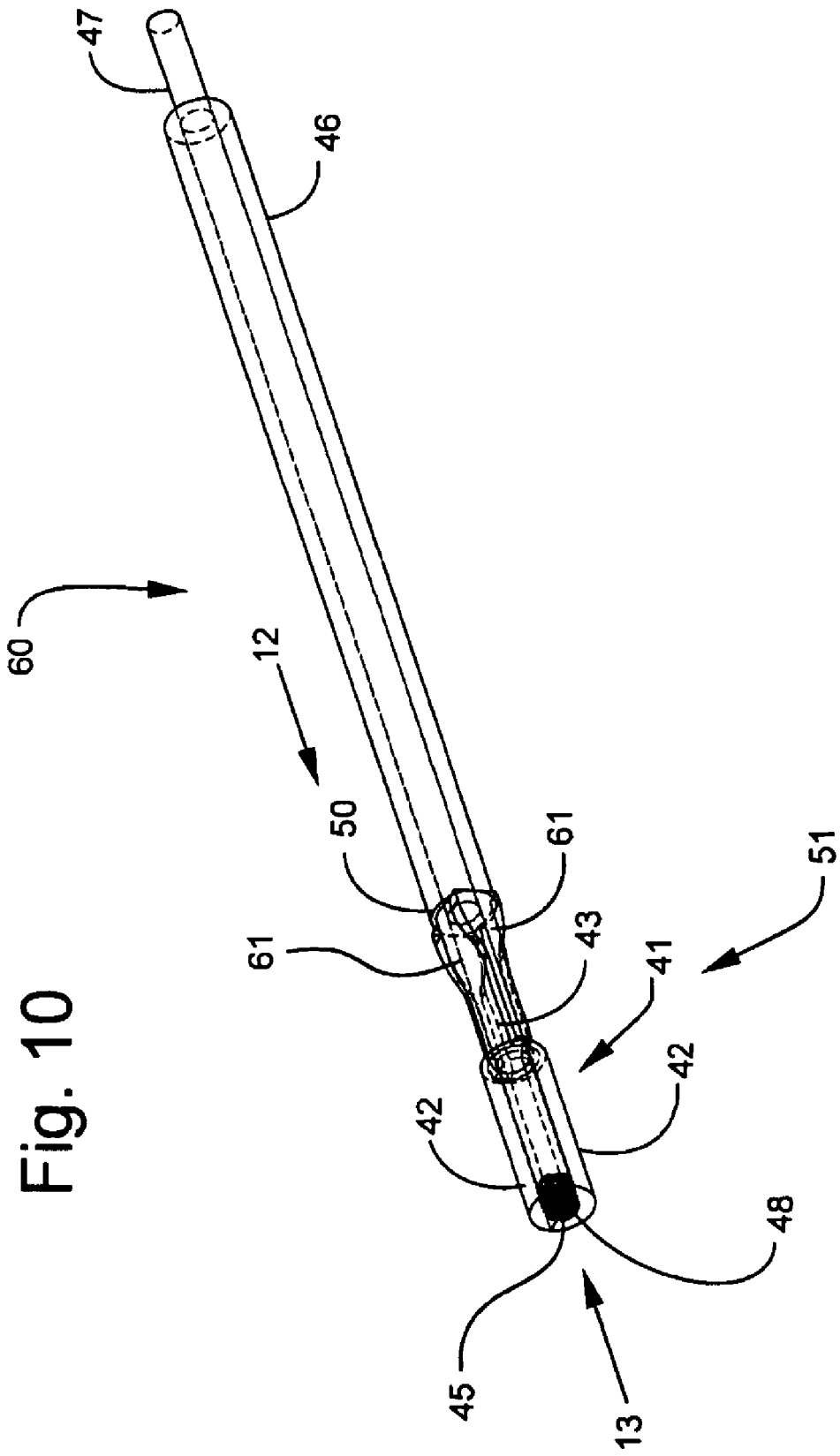
FIG. 10 is a perspective view of a bone fusion device having outer expandable members and an inner expander having flared proximal portions lockable with the proximal portion of the expandable members to lock the expandable members in an expanded configuration in an embodiment of the present invention.
Figure 11:
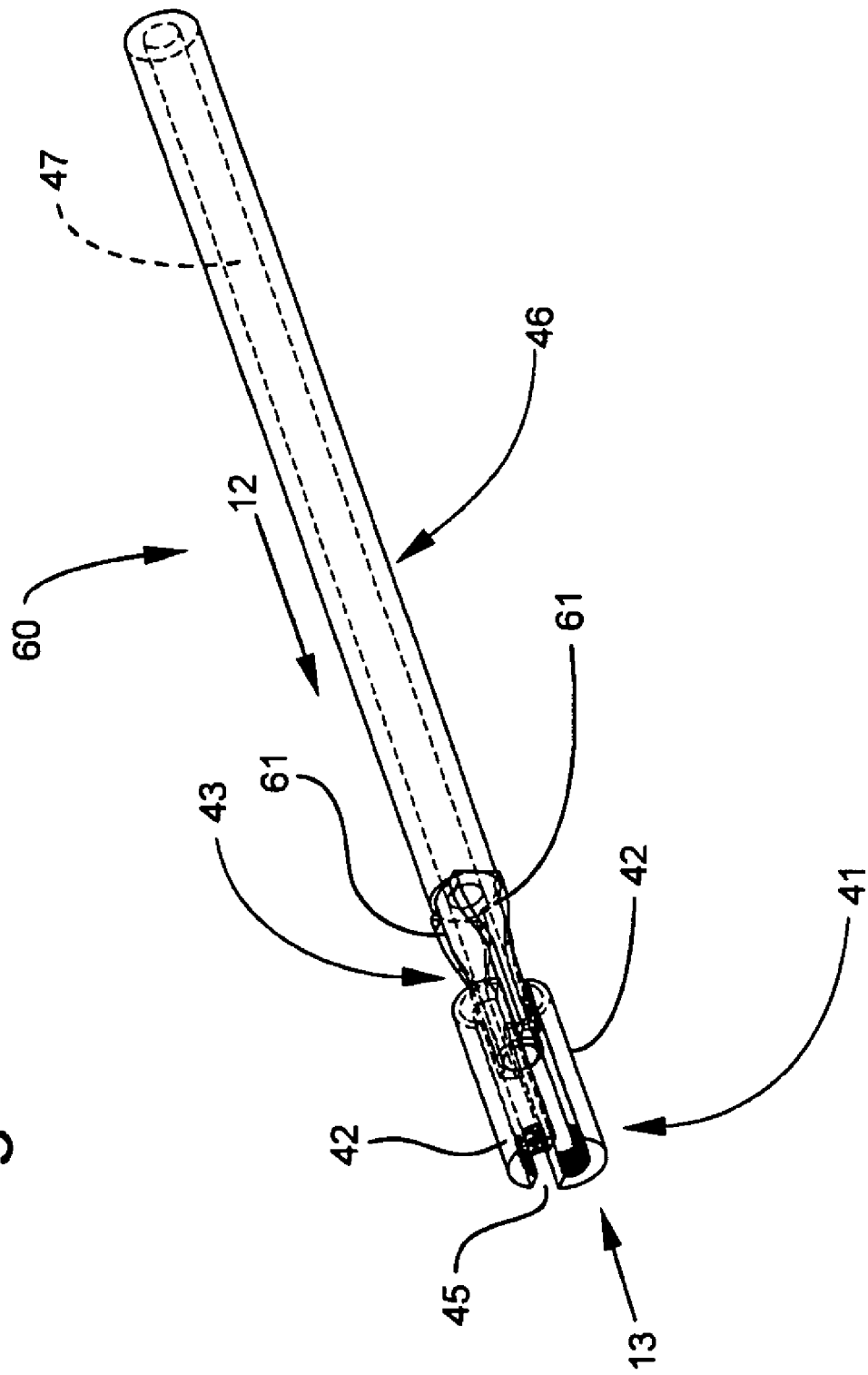
FIG. 11 is a perspective view of the bone fusion device shown in FIG. 10, showing the outer expandable members partially expanded and the inserted inner expander partially inserted into the outer expandable members in an embodiment of the present invention.
Figure 12:
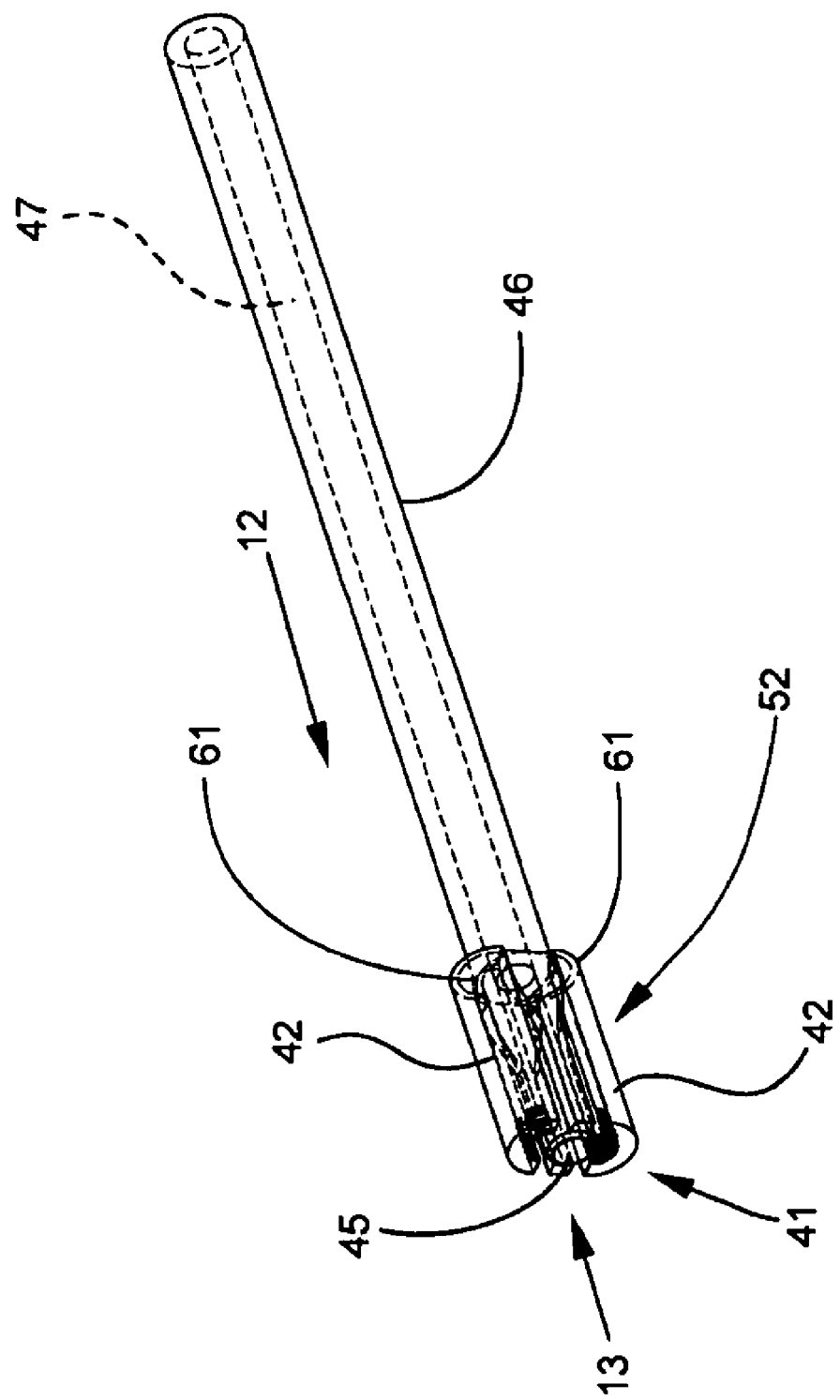
FIG. 12 is a perspective view of the bone fusion device shown in FIG. 10, showing the outer expandable members expanded and locked by the inner expander fully inserted into the outer expandable members in an embodiment of the present invention.
Figure 13:
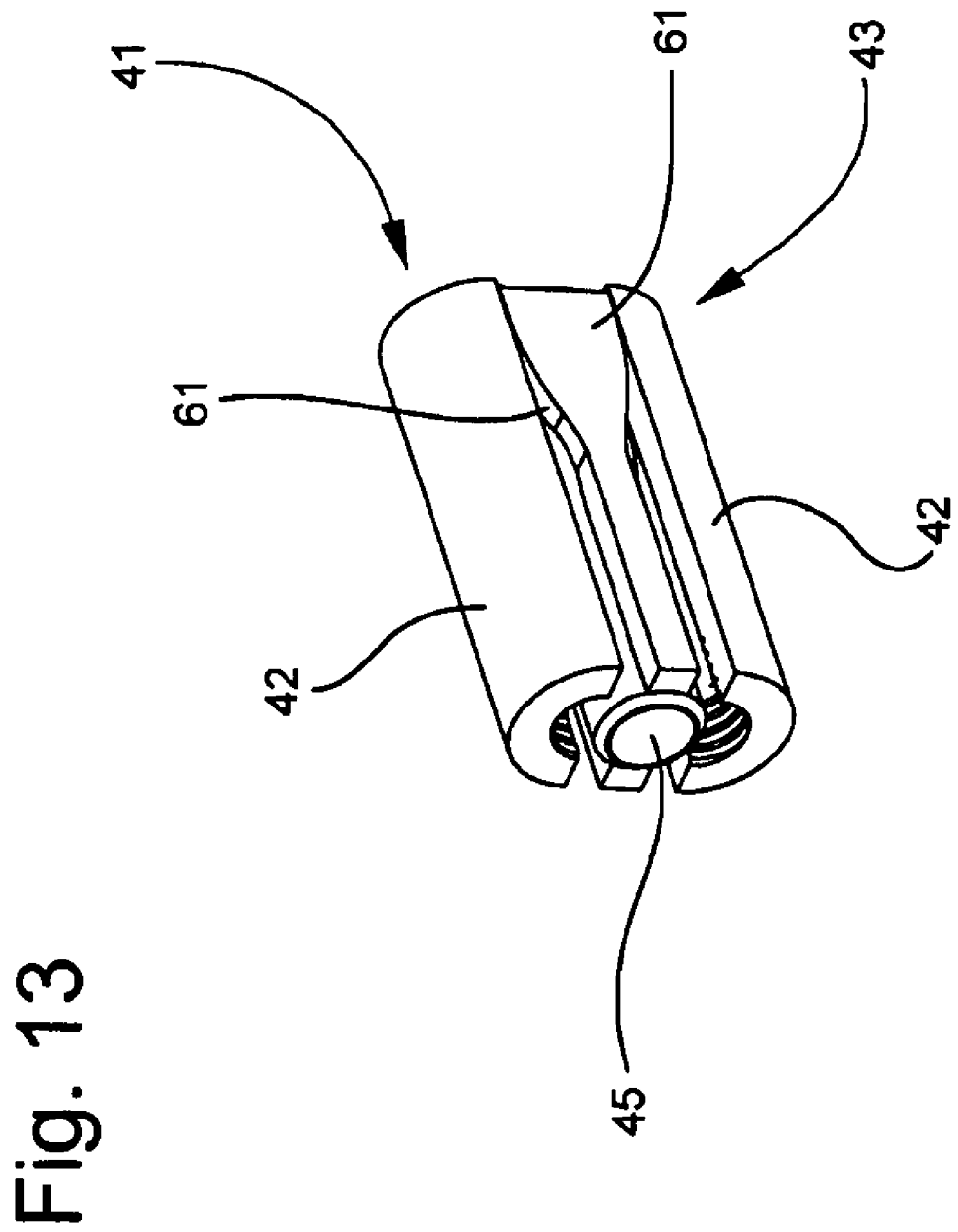
FIG. 13 is a perspective view of the fully expanded outer expandable members and the fully inserted inner expander in an embodiment of the present invention.

As shown in FIGS. 5, 7, and 9, in some embodiments, the engaging outer surface portions of the inner expander 43 can comprise a plurality of ribs, or locking flanges 44, extending outwardly from the outer surface of the inner expander 43. The inner expander 43 can include at least one locking flange 44 for interlocking with each outer expandable member 42. For example, in the embodiments in FIGS. 5-9, the outer expandable component 41 can include four outer expandable members 42 having the shape of a cylinder, and the inner expander 43 includes four locking flanges 44. In certain embodiments, the number of outer expandable members 42 can be varied to change the expanded geometry of the bone fusion device 40. Each of the outer expandable members 42 can include a locking channel 53 configured to matingly interlock with one of the locking flanges 44 projecting from the inner expander. As the inner expander 43 is translated forward by the pushing tube 46, the locking flanges 44 on the inner expander 43 can engage the locking channels 53 in the outer expandable members 42 and slide longitudinally along the locking channels 53. As the inner expander 43 moves from the proximal end 12 to the distal end 13 of the outer expandable component 41, the outer expandable members 42 expand outwardly away from each other and into a desired configuration in contact with the adjacent vertebral bodies 96. When the inner expander 43 is fully translated into the outer expandable component 41, the outer expandable members 42 can be fully expanded into the expanded configuration 52. In the expanded configuration 52, the inner expander 43 and the outer expandable members 42 can be completed locked together.

Once the outer expandable component 41 is properly positioned in the intervertebral space 97 and prior to the outer expandable members 42 being expanded, the inner rod 47 can be detached from the outer expandable members 42. When the outer expandable members 42 are expanded into the expanded configuration 52, the pushing tube 46 can be detached from the inner expander 43. Both the inner rod 47 and the pushing tube 46 can then be removed from the surgical site, leaving the expanded bone fusion device 40 in secure position between the vertebral bodies 96.

In some embodiments of the bone fusion device 40, the interlockable flanges 44 on the inner expander 43 and the mating flange channels 53 in the outer expandable members 42 can comprise characteristics that are sufficient to maintain the inner expander 43 and each of the outer expanding members 42 locked together for the functional life of the device 40. Such characteristics can include, for example: a mating configuration resistant to dislodgement; a narrow fit tolerance for providing a tight fit between the interlockable flanges 44 and the flange channels 53; material(s) having sufficient tensile strength to accommodate loads placed on the device 40 by the compressive force transmitted by the vertebrae 96; and surfaces that resist movement of the flanges 44 and flange channels 53 once they are interlocked in the intervertebral space 97.

In some embodiments, the inner expander 43 can have the open lumen 45 to allow insertion of bone growth promoting material through the lumen 45. When the inner rod 47 and the pushing tube 46 are removed from the implanted bone fusion device 40, bone growth promoting material can be inserted into the inner expander lumen 45. In certain embodiments, the walls of the inner expander 43 and the walls of the outer expandable members 42 can include bone growth openings 55 to allow for interaction of bone graft packed inside with the adjacent endplates 93 so as to promote bone fusion.

Some embodiments of the present invention can be inserted into the intervertebral space 97 using a small percutaneous access opening via a minimally invasive procedure. Thus, such a bone fusion device 40 can be inserted into the intervertebral space 97 at a first smaller dimension and deployed to a second, larger dimension to occupy the intervertebral space 97. In this manner, unnecessary distraction of the vertebral bodies 96 and surrounding tissues (for example, neural and vascular tissues) can be avoided.

The expansion member 43 serves to transition the outer expandable members 42 of the bone fusion device 40 from the initial, unexpanded configuration 51 toward the expanded configuration 52, as shown in FIG. 8. The inner expander 43 and the outer expandable members 42 of the bone fusion device 40 can be configured to expand along the first transverse axis 24 to distract the vertebrae 96 and/or to restore and/or maintain normal spinal curvature between the adjacent vertebral bodies 96. Additionally, the inner expander 43 and the outer expandable members 42 can be configured to expand along the second transverse axis 25 generally perpendicular to the first axis 24 to distribute loading of the bone fusion device 40 across a larger and more dispersed area of the adjacent vertebral endplates 93. In this manner, the device 40 can provide improved stability of the device 40 between the adjacent vertebral bodies 96 and/or an increased resistance to subsidence of the device 40 into the vertebral bodies 96.

The outer expandable members 42 and the inner expander 43 can have various cross-sectional configurations. In the embodiments shown in FIGS. 5-9, the outer and inner member cross-sections are circular. However, in certain embodiments, the outer and inner members 42, 43, respectively, can have cross-sections that are rectangular, oval, or other suitable configurations for maintaining a desired intervertebral space 97 between adjacent vertebral bodies 96.

The adjacent vertebral bodies 96 can transmit a significant compressive force onto the outer expandable members 42 in the intervertebral space 97. Some embodiments of the bone fusion device 40 can include features that facilitate insertion of the inner expander 43 into the outer expandable members 42 so as allow such compressive force to be overcome without difficulty. For example, the inner expander 43 can have an outer surface comprising material(s) and/or treatment that allow the inner expander 43 to be inserted into the outer expandable members 42 without excessive force. In addition, in some embodiments, the inner expander 43 can have a configuration relative to the outer expandable members 42 (for example, the same configuration) that minimizes the mechanical advantage required to translate the pushing tube 46 and the attached inner expander 43 forward into the outer expandable members 42.

In some embodiments, the bone fusion device 10 can include a tapered distal end 56, or "nose," on the outer expandable component 41 to facilitate insertion of the device 40 into the target intervertebral space 97. Some embodiments of the bone fusion device 40 can include the taper 56 to provide a desired degree of angulation between the adjacent bones. In the case of embodiments for use in an intervertebral joint 97, the angle provided can be between about 0 degrees and 25 degrees.

Once natural disc material is removed prior to spinal fusion, the normal lordotic or kyphotic curvature of the spine 90 can be reduced or eliminated. Some embodiments of the bone fusion device 40 can expand linearly in a vertical direction between adjacent vertebral bodies 96 without also expanding laterally or changing position. As a result, the device 40 can take up less space when deployed, positioning of the device 40 relative to the vertebral bodies 96 can be controlled, and fixation of the implanted device 40 can be stabilized. In other embodiments, the implanted bone fusion device 40 can provide expansion along two transverse dimensions 24, 25. For example, in some embodiments, the bone fusion device 40 can expand both along the height (or vertical transverse dimension 24) of the intervertebral disc space 97 to help maintain and/or restore the natural anatomy of a fused spinal vertebrae. In addition, the device 40 may expand in a lateral direction (or horizontal transverse dimension 25) so as to provide a larger overall area for absorbing and/or distributing vertebral loads, thereby improving stability and/or resistance to subsidence of the device 40 into the adjacent vertebral bodies 96. In particular embodiments, the rate of expansion along the transverse axes 24, 25 need not necessarily be equal. Instead, the inner expander 43 and the outer expandable members 42 may be configured to provide unequal or varying rates of expansion along the transverse axes 24, 25. In some embodiments, insertion and expansion of the inner expander 43 can provide uniform expansion of the outer expandable members 42 along the longitudinal axis 21 of the device 40.

Embodiments of the bone fusion device 10 of the present invention can have various shapes. For example, the outer expanding component 41 can have a substantially cylindrical shape, as shown in FIGS. 5-9. Alternatively, the outer expanding component 41 can have a substantially rectangular shape, hourglass shape, or other shape suitable for interfacing with a vertebral body 96 for maintaining a desired intervertebral space 97 between adjacent vertebral bodies 96. The geometries of the outer expandable members 42 and the inner expander 43 can be varied to optimize expanded bone fusion implant 40 size and shape.

The outer expandable members 42 can comprise an outer contact surface configured to have a surface area to distribute the disc space load on the bone fusion device 40 across a large region of the vertebral bodies 96. In some embodiments, the outer contact surface of the outer expandable members 42 can be substantially flat. In other embodiments, the contact surface may be rounded. In some embodiments, the contact surface may be the entire width of the bone fusion device 40. In other embodiments, the contact surface may have a width less than the width of the entire bone fusion device 40.

In various embodiments of the bone fusion device 40, the outer wall can comprise various surface configurations, as describe herein. For example, some surface configurations can include bone anchoring elements (not shown) adapted for engagement with adjacent vertebral bodies 96 to prevent or inhibit movement of the bone fusion device 40 once implanted within the intervertebral disc space 97.

Such embodiments of the bone fusion device 40 having outer expandable members 42 and the inner expander 43 have advantages over conventional bone fusion devices. For example, the outer expandable members 42 can be inserted in the collapsed, or unexpanded, configuration 51 into a space between bones, thereby allowing insertion using a minimally invasive surgical procedure. Such a device 40 can engage adjacent bones, such as vertebral bodies 96, in such a manner as to be self-stabilizing. As a result, such embodiments provide for maintaining appropriate intervertebral spacing and stabilization of the vertebrae 96 during the fusion process.

Some embodiments of the bone fusion device 40 may be utilized in an intervertebral space 97 in which there is normally a lordotic (anterior) curve, such as in the lumbar spine, or in an intervertebral space 97 in which there is normally a kyphotic (posterior) curve, such as in the thoracic spine. When diseased or damaged natural disc material is removed, the normal lordotic or kyphotic curvature of the spine 90 can be disadvantageously reduced or eliminated. Some embodiments of the bone fusion device 40 having outer expandable members 42 and the inner expander 43 can help maintain and/or restore the natural anatomy of the fused spinal vertebreae 96. For example, the inner expander 43 and/or the outer expandable members 42 can be tapered along the longitudinal axis 21 of the device 40 so as to provide a desirable lordotic or kyphotic curve in the implanted intervertebral disc space 97.

The present invention can include embodiments of a bone fusion system and/or a bone fusion device kit. Such a system and/or kit can include embodiments of the bone fusion device 40 as described herein. For example, the bone fusion device 40 can include the outer expandable component 41 having a plurality of outer expandable members 42 insertable to a surgical site in the unexpanded, configuration 51. The inner expander 43 having an outer dimension larger than the inner dimension of the outer expandable component 41 can be inserted in the outer expandable component 41 and moved from the proximal end 12 toward the distal end 13 of the outer expandable component 41 to expand the outer expandable members 42 into the expanded configuration 52. The inner expander 43 can include outer surface engaging portions that can interlock with inner surface engaging portions in the outer expandable members 42 such that the inner expander 43 remains locked together with the expanded outer expanding members 42 in the expanded configuration 52. Axial displacement of the outer expandable members 42 along the longitudinal axis 21 causes the outer members 42 to separate from each other, thereby transitioning the bone fusion device 40 to the expanded configuration 52. In some embodiments, the outer expandable members 42 can separate completely from each other. The bone fusion device 40 can be delivered to a surgical site, for example, in the intervertebral space 97 between adjacent vertebral bodies 96, utilizing a minimally invasive procedure.

In some embodiments, the bone fusion system and/or a bone fusion device kit can further include the inner rod 47 that can be detachably attached to the distal end 13 of the outer expandable component 41. In some embodiments, the bone fusion system and/or a bone fusion device kit can further include the pushing tube 46 that can be detachably attached to the proximal end 12 of the inner expander 43. The inner expander 43 and the attached pushing tube 46 can be slid over the inner rod 47 so that the distal end 13 of the inner expander 43 can engage the proximal end 13 of the outer expandable component 41. While the outer expandable component 41 can be held in a desired position in, for example, the intervertebral space 97, with the inner rod 47, the pushing tube 46 can be translated forward to push the inner expander 43 inside the outer expandable component 41. In this way, the inner expander 43 can cause the outer expandable members 42 to move outwardly and apart from each other.

In some embodiments, the engaging outer surface portions of the inner expander 43 can comprise a plurality of ribs, or locking flanges 44, extending outwardly from the outer surface of the inner expander 43. Each of the outer expandable members 42 can include the locking channel 53 configured to matingly interlock with one of the locking flanges 44 projecting from the inner expander 43. As the inner expander 43 is translated forward by the pushing tube 46, the locking flanges 44 on the inner expander 43 can engage the locking channels 53 in the outer expandable members 42 and slide longitudinally along the locking channels 53. As the inner expander 43 moves from the proximal end 12 to the distal end 13 of the outer expandable component 41, the outer expandable members 42 can expand outwardly away from each other and into a desired configuration in contact with the adjacent vertebral bodies 96. When the inner expander 43 is fully translated into the outer expandable component 41, the outer expandable members 42 can be fully expanded into the expanded configuration 52. In the expanded configuration 52, the inner expander 43 and the outer expandable members 42 can be completed locked together.

The present invention can include embodiments of a method for fusing bone. Such a method can comprise utilizing the bone fusion device 40, system, and/or kit as described herein. For example, one such method can include providing the bone fusion device 40 including the outer expandable component 41 having a plurality of outer expandable members 42 insertable to a surgical site in the unexpanded, configuration 51. The inner expander 43 having an outer dimension larger than the inner dimension of the outer expandable component 41 can be inserted in the outer expandable component 41 and moved from the proximal end 12 toward the distal end 13 of the outer expandable component 41 to expand the outer expandable members 42 into the expanded configuration 52. The inner expander 43 can include engaging outer surface portions that can interlock with engaging inner surface portions in the outer expandable members 42 such that the inner expander 43 remains locked together with the expanded outer expanding members 42 in the expanded configuration 52. Axial displacement of the outer expandable members 42 along the longitudinal axis 21 causes the outer members 42 to separate from each other, thereby transitioning the bone fusion device 40 to the expanded configuration 52. In some embodiments, the outer expandable members 42 can be completely separated from each other. The bone fusion device 40 can be delivered to a surgical site, for example, in the intervertebral space 97 between adjacent vertebral bodies 96, utilizing a minimally invasive procedure.

In another aspect of the present invention, some embodiments of the bone fusion device 60 can comprise the outer expandable component 41 having a plurality of outer expandable members 42 insertable to a surgical site in the collapsed, or unexpanded, configuration 51. The inner expander 43 can be inserted in the outer expandable component 41 and moved from the proximal end 12 toward the distal end 13 of the outer expandable component 41 to expand the outer expandable members 42 into the expanded configuration 52. The inner expander 43 can include an outwardly flared proximal portion 61 that can interlock with the proximal end 13 of the outer expandable members 42 such that the inner expander 43 remains locked together with the expanded outer expanding members 42 in the expanded configuration 52. The bone fusion device 60 can be delivered to a surgical site, for example, in the intervertebral space 97 between adjacent vertebral bodies 96, utilizing a minimally invasive procedure.

As shown in the embodiments in FIGS. 10-13, the bone fusion device 60 can include a plurality of cooperating outer expandable members 42 that in the collapsed, unexpanded configuration 51 together comprise a hollow lumen 45 extending along the longitudinal axis 21 of the device 60. In some embodiments, the lumen 45 of the outer expandable members 42 can be sized and configured to receive the inner expander 43 therein. The relationship of the size and configuration of the outer expandable members 42 and the inner expander 43 can be such that movement of the inner expander 43 within the lumen 45 of the outer expandable component 41 engages the outer expandable members 42 to expand along the longitudinal axis 21 of the device 60. As a result, axial displacement of the outer expandable members 41 along the longitudinal axis 21 causes the outer expandable members 42 to separate from each other, thereby transitioning the bone fusion device 60 to the expanded configuration 52. In some embodiments, the outer expandable members 42 can separate completely from each other.

In some embodiments, the bone fusion device 60 can further include the inner rod 47 that can be detachably attached to the outer expandable component attachment point 48 on the distal end 13 of the outer expandable component 41. In some embodiments, attachment of the inner rod 47 to the distal end 13 of the outer expandable component 41 can be a threaded attachment. In other embodiments, attachment of the inner rod 47 to the distal end 13 of the outer expandable component 41 can be any other suitable method of releasable attachment.

In some embodiments, the bone fusion device 60 can further include the pushing tube 46 that can be detachably attached to the inner expander attachment point 50 on the proximal end 13 of the inner expander 43. In some embodiments, attachment of the pushing tube 46 to the inner expander 43 can be an abutting attachment, or engagement. In other embodiments, attachment of the pushing tube 46 to the inner expander 43 can be threaded engagement or any other suitable method of releasable attachment. The inner expander 43 and the attached pushing tube 46 can be slid over the inner rod 47 so that the distal end 13 of the inner expander 43 can engage the proximal end 13 of the outer expandable component 41. The inner expander 43 can have an outside dimension in its proximal 13 portion larger than the inside dimension of the outer expandable component 41. While the outer expandable component 41 can be held in a desired position in, for example, the intervertebral space 97, with the inner rod 47, the pushing tube 46 can be translated forward to push the inner expander 43 inside the outer expandable component 41. In this way, the inner expander 43 can cause the outer expandable members 42 to move outwardly and apart from each other. As the outer expandable members 42 are expanded apart, they can contact the adjacent vertebral body endplates 93.

Once the outer expandable component 41 is properly positioned in the intervertebral space 97 and prior to the outer expandable members 42 being expanded, the inner rod 47 can be detached from the outer expandable members 42. When the outer expandable members 42 are expanded into the expanded configuration 52, the pushing tube 46 can be detached from the inner expander 43. Both the inner rod 47 and the pushing tube 46 can then be removed from the surgical site, leaving the expanded bone fusion device 60 in secure position between the vertebral bodies 96.

In one embodiment, as shown in FIGS. 10-13, the inner expander 43 can be flared outwardly (61) near its proximal end 13 toward each of the outer expandable members 42. Although the embodiments in FIGS. 10-13 show two outer expandable members 42 and two directions of flaring of the inner expander 43 proximal portion, in embodiments having more than two outer expandable members 42, the inner member 43 can flare outwardly toward each of the outer expandable members 42. The distance the proximal 12 portion of the inner expander 43 is flared can be sufficient to wedge the inner expander 43 between the fully expanded segments of the outer expandable members 42. The pressure of the flared proximal portion 61 of the inner expander 43 wedged against the inside surface of the expanded outer expandable members 42 can be sufficient to hold the outer expandable members 42 in position against the adjacent vertebral bodies 96. In this manner, the outwardly flared proximal portion 61 of the inner expander 43 can cause the inner expander 43 to be retained within the outer expandable members 42 in the expanded configuration 52. Accordingly, such flaring of the proximal portion 61 of the inner expander 43 can comprise a retention element.

In some embodiments, the retention element can comprise other configurations (not shown). For example, one of the inner expander 43 or the outer expandable members 42 can include one or more projections near its proximal end 12 extending inwardly toward the other component. The other component can include a corresponding number of receptacles for receiving the projections when the inner expander 43 is fully inserted into the outer expandable members 42. The receptacle(s) may be, for example, a hole, notch, depression, or other structure for securely receiving the projection. The pressure exerted by the adjacent vertebral bodies 96 onto the expanded outer expandable members 42 and onto the inner expander 43 may be sufficient to cause the projection to seat into the corresponding receptacle. Alternatively, the projection may be biased, for example, with a spring, toward the receptacle in the opposing inner or outer component surface. In certain embodiments, the retention mechanism can include one or more projections extending inwardly from the inner expander 43, for example, near the proximal end 13 of the inner expander 43, that are keyed to lock into a correspondingly keyed receptacle or structure in one or more of the outer expandable members 42. When the inner expander 43 is fully inserted into the outer expandable members 42 and the outer expandable members 42 are fully expanded, the inner expander 43 can be rotated so as to lock the projecting structure(s) into the corresponding receiving structure in the outer expandable members 42.

In other embodiments, the retention mechanism can comprise one or more angled teeth (not shown), or inclined ramps, near the proximal end 12 of the bone fusion device 60 and extending inwardly from the surface of each of the inner expander 43 and the outer expandable members 42. The teeth can be angled toward the distal end 13 of the inner expander 43 and the outer expandable members 42. As the inner expander 43 is translated axially into the outer expandable members 42 to expand the outer expandable members 42, the teeth of the inner expander 43 and the teeth of the outer expandable members 42 can engage each other. When the inner expander 43 is fully inserted into the outer expandable members 42 and the outer expandable members 42 are fully expanded, the teeth of each of the inner expander 43 and the outer expandable members 42 can be fully engaged with each other such that the inner expander 43 is retained within the expanded outer expandable members 42. In certain embodiments, the teeth extending inwardly from the inner expander 43 and the outer expandable members 42 toward each other can be located along the longitudinal axis 21 of the device 60.

In particular embodiments, the retention mechanism can include both outward flaring 61 of the inner expander 43 near its proximal end 12 toward each of the outer expandable members 42 and a projection and receptacle component, mating teeth, or other structures for locking the inner expander 43 into position with the expanded outer expandable members 42. In this manner, the retention mechanism can cause the inner expander 43 to be retained within the outer expandable members 42 in the expanded configuration 52, thereby helping to maintain the outer expandable members 42 in the expanded configuration 52 and in a desired position relative to the adjacent vertebral bodies 96.

The present invention can include embodiments of a bone fusion system, a bone fusion device kit, and/or method for fusing bone. Such a system and/or kit can include embodiments of the bone fusion device 60, as described herein. For example, the bone fusion device 60 can include the outer expandable component 41 having a plurality of outer expandable members 42 insertable to a surgical site in the collapsed, or unexpanded, configuration 51. The inner expander 43 can be inserted into the outer expandable component 41 and moved from the proximal end 12 toward the distal end 13 of the outer expandable component 41 to expand the outer expandable members 42 into the expanded configuration 52. The inner expander 43 can include an outwardly flared proximal portion 61 that can interlock with the proximal end 12 of the outer expandable members 42 such that the inner expander 43 remains locked together with the expanded outer expanding members 42 in the expanded configuration 52. The bone fusion device 60 can be delivered to a surgical site, for example, in the intervertebral space 97 between adjacent vertebral bodies 96, utilizing a minimally invasive procedure. Axial displacement of the outer expandable members 42 along the longitudinal axis 21 causes the outer expandable members 42 to separate from each other, thereby transitioning the bone fusion device 60 to the expanded configuration 52. In some embodiments, the outer expandable member 42 can separate completely from each other.

In some embodiments, the bone fusion device 60 can further include the inner rod 47 that can be detachably attached to the outer expandable component attachment point 48 on the distal end 13 of the outer expandable component 41. In some embodiments, the bone fusion device 60 can further include the pushing tube 46 that can be detachably attached to the inner expander attachment point 50 on the proximal end 12 of the inner expander 43. The inner expander 43 and the attached pushing tube 46 can be slid over the inner rod 47 so that the distal end 12 of the inner expander 43 can engage the proximal end 12 of the outer expandable component 41. The inner expander 43 can have an outside dimension in its proximal portion 12 larger than the inside dimension of the outer expandable component 41. While the outer expandable component 41 can be held in a desired position with the inner rod 47, the pushing tube 46 can be translated forward to push the inner expander 43 inside the outer expandable component 41. In this way, the inner expander 43 can cause the outer expandable members 42 to move outwardly and apart from each other. As the outer expandable members 42 are expanded apart, they can contact the adjacent vertebral body endplates 93.

In another aspect of the present invention, some embodiments of the bone fusion device can comprise the outer expandable component 41 including a plurality of outer expandable members 42 connected by a locking mechanism. Such a bone fusion device 70 can be delivered to a site between bones in the collapsed, or unexpanded, configuration 51 in a minimally invasive manner. When in the target site, for example, the intervertebral space 97, the outer expandable members 42 can be expanded into the expanded configuration 52 using an expandable body 71 and locked into position with the locking mechanism.

Figure 14:
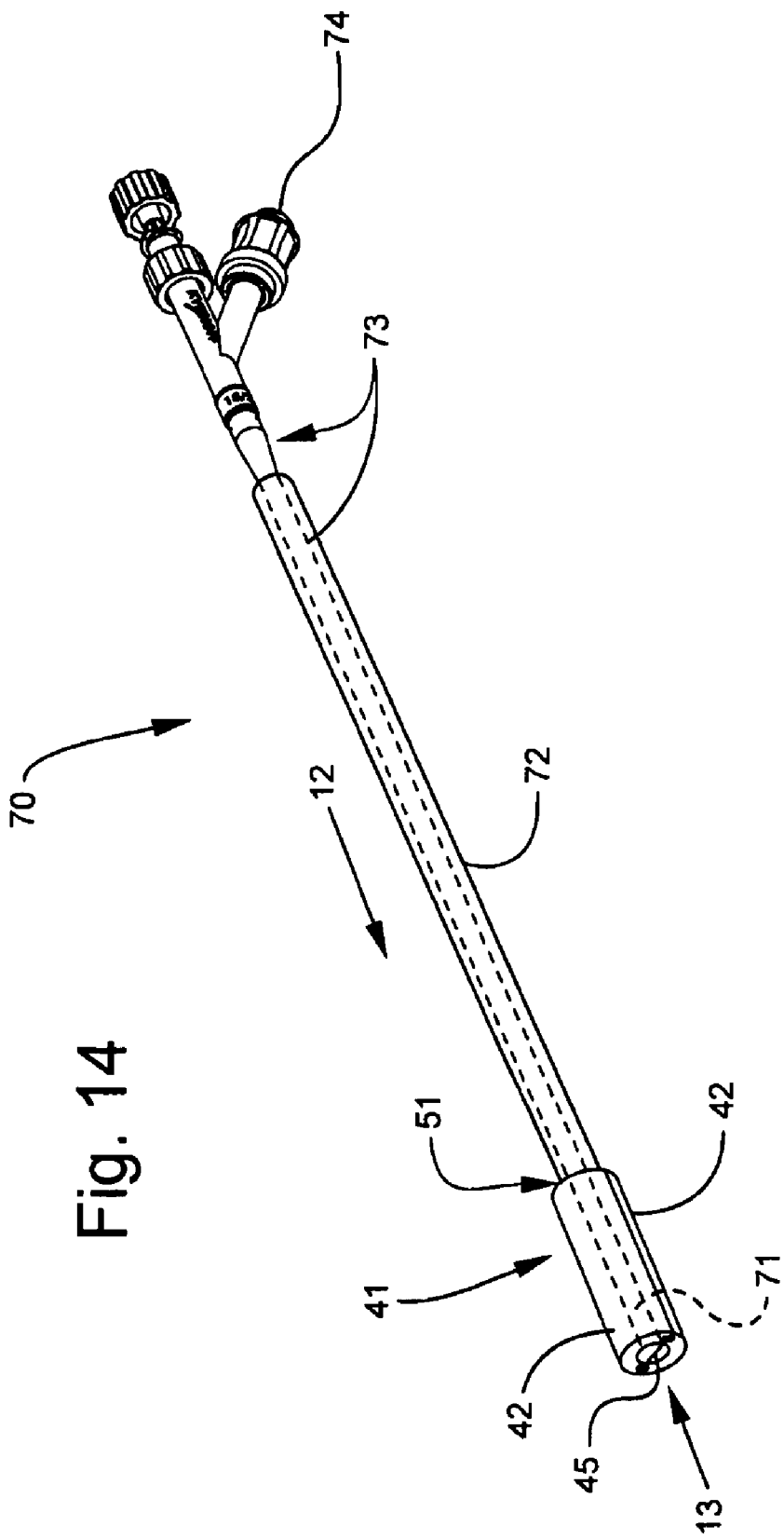
FIG. 14 is a perspective view of a bone fusion device having an outer expandable component comprising a plurality of outer expandable members and two locking bridges, a delivery cannula, an expandable body, and a catheter tube for inserting the expandable body into the outer expandable component, showing the device in unexpanded configuration in an embodiment of the present invention.
Figure 15:
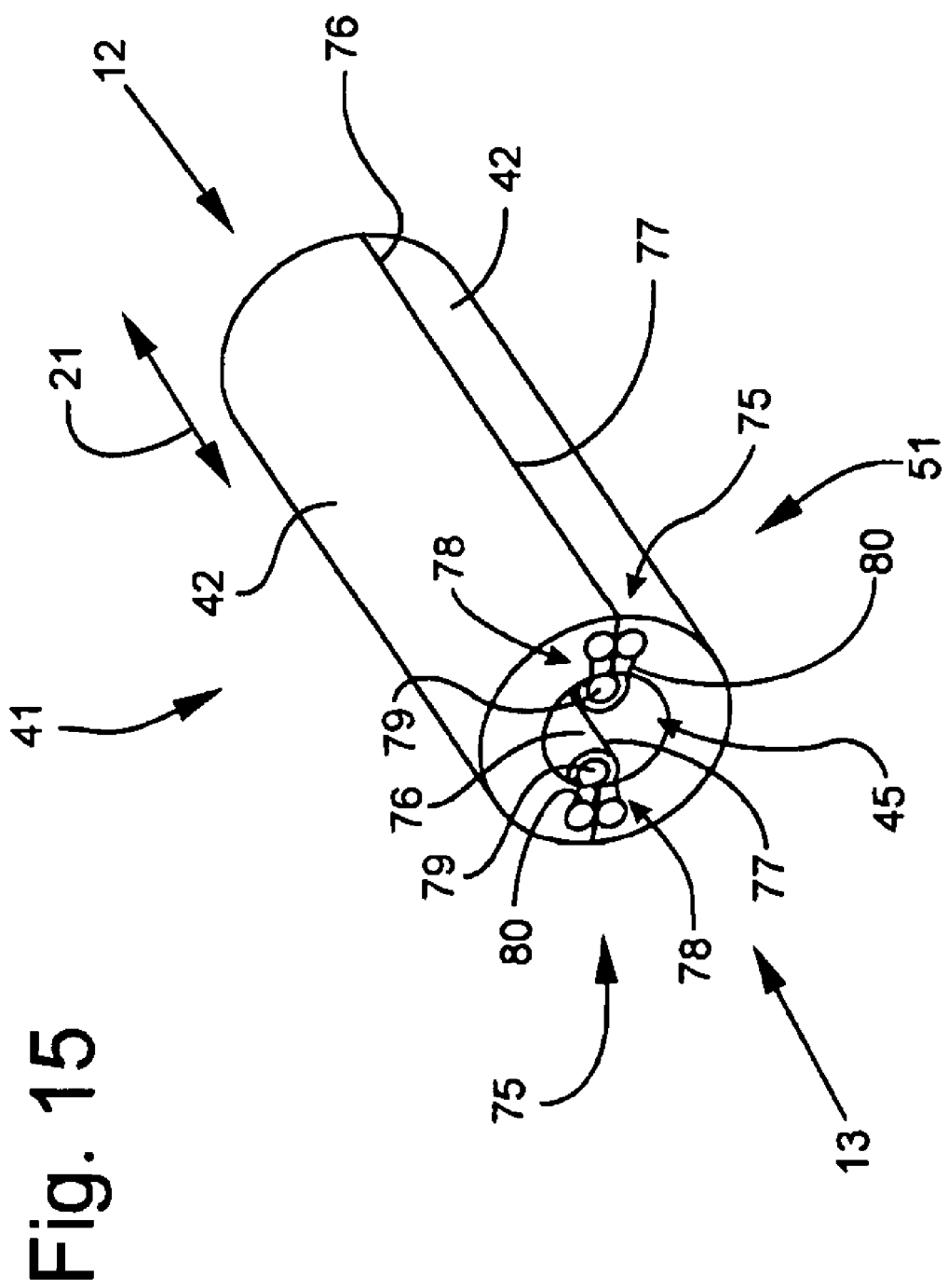
FIG. 15 is a perspective view of the outer expandable component comprising outer expandable members and two locking bridges shown in FIG. 14, in an embodiment of the present invention.

Some embodiments of the bone fusion device 70 can include a plurality of the outer expandable members 42. As shown in the illustrative embodiment in FIGS. 14-17, the bone fusion device 70 can include two outer expandable members 42. In other embodiments, the bone fusion device 70 can include more than two of the outer expandable members 42, for example, three, four, or more of the expandable members 42. The desired number of expandable members 42 can depend on various factors, including, for example, the normal and current anatomy of the bones to be fused, the distance between the bones to be fused, the materials comprising the outer expandable members 42 and the locking mechanism, and the surgical approach for inserting the device 70. Each of the outer expandable members 42 can be separable from each other expandable member 42. As shown in FIGS. 14 and 15, in the unexpanded state, or configuration 51, the bone fusion device 70 can comprise a closed cylindrical, or tubular, configuration having a longitudinal axis 21. The outer expandable component 41 can have any unexpanded configuration suitable for insertion between adjacent bones by a small diameter, elongate delivery shaft (for example, the delivery tube 72) via a minimally invasive procedure. For example, the unexpanded configuration 51 of the outer expandable component 41 can be round, oval, rectangular, or other tubular shape.

Each of the outer expandable members 42 can include a side 76 along a cross-section of the walls of the members 42. In the unexpanded configuration 51, one side 76 of each of the outer expandable members 42 can be in contact with one side 76 of another expandable member 42 at an expandable member interface 77. The expandable member interfaces 77 can extend along the longitudinal axis 21 of the device 70. In this way, the device 70 can be maintained in its smallest outside dimension (for example, diameter) for insertion into the intervertebral space 97 in a minimally invasive manner.

In some embodiments, one side 76 of each of the plurality of outer expandable members 42 can be connected to one side 76 of another expandable member 42 by the locking mechanism. The locking mechanism can be capable of locking the connected outer expandable members 42 in the expanded configuration 52. In some embodiments, as shown in FIGS. 14-17, the locking mechanism can comprise a movable locking bridge 75, which can extend along the interfacing sides 76 along the length of the outer expandable component 41. In some embodiments, the locking bridge 75 can comprise a separate, independent locking bridge 75 between the sides 76 of the outer expandable members 42 along each expandable member interface 77. For example, in the embodiment shown in FIGS. 14-17, the outer expandable component 41 can include two outer expandable members 42, and the device 70 can include two locking bridges 75, one locking bridge 75 connecting each of two opposing sides 76 of the expandable members 42.

Figure 16:
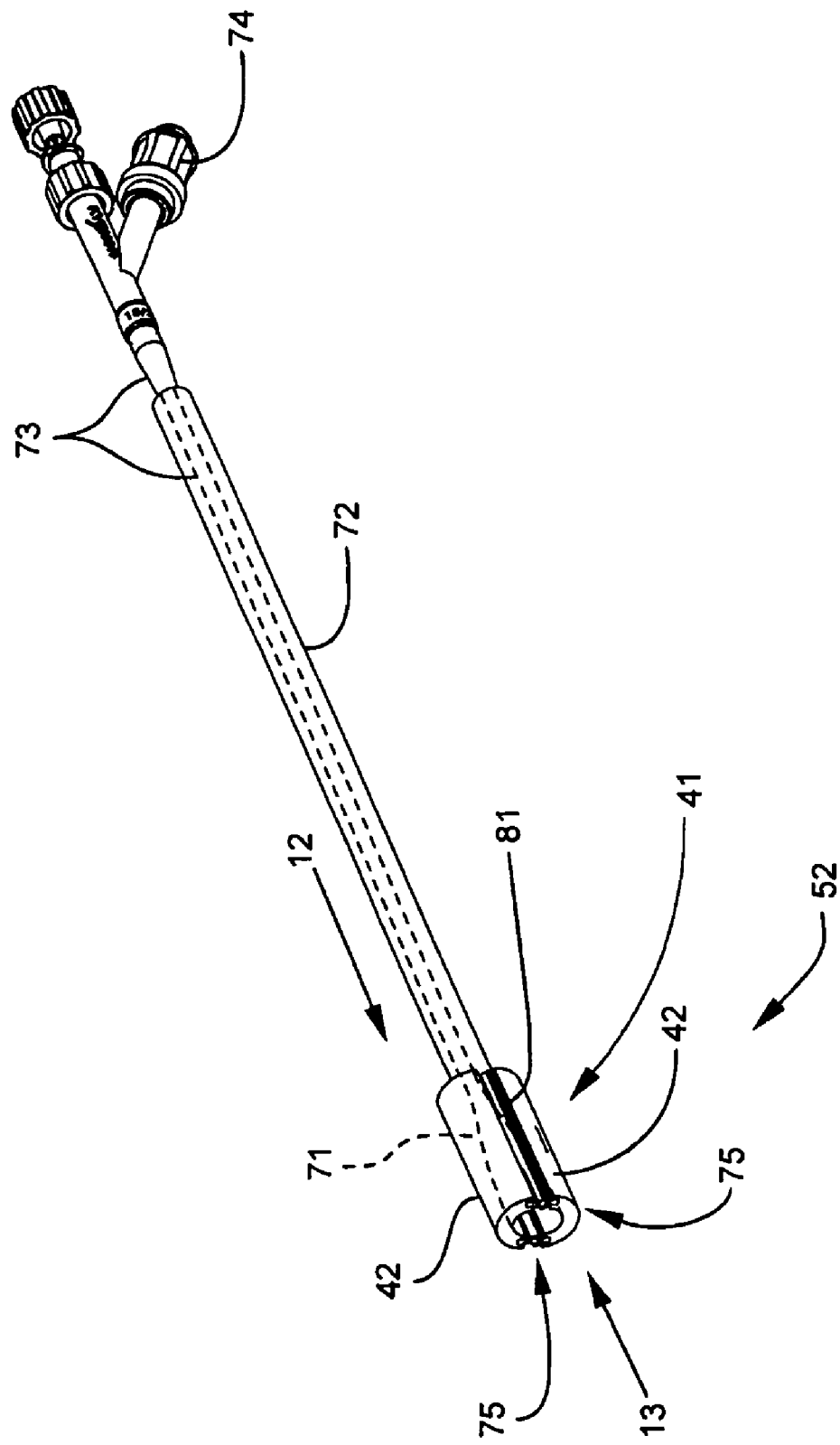
FIG. 16 is a perspective view of the bone fusion device in FIG. 14, showing the outer expandable members expanded into the expanded configuration by the expandable body, in an embodiment of the present invention.
Figure 17:
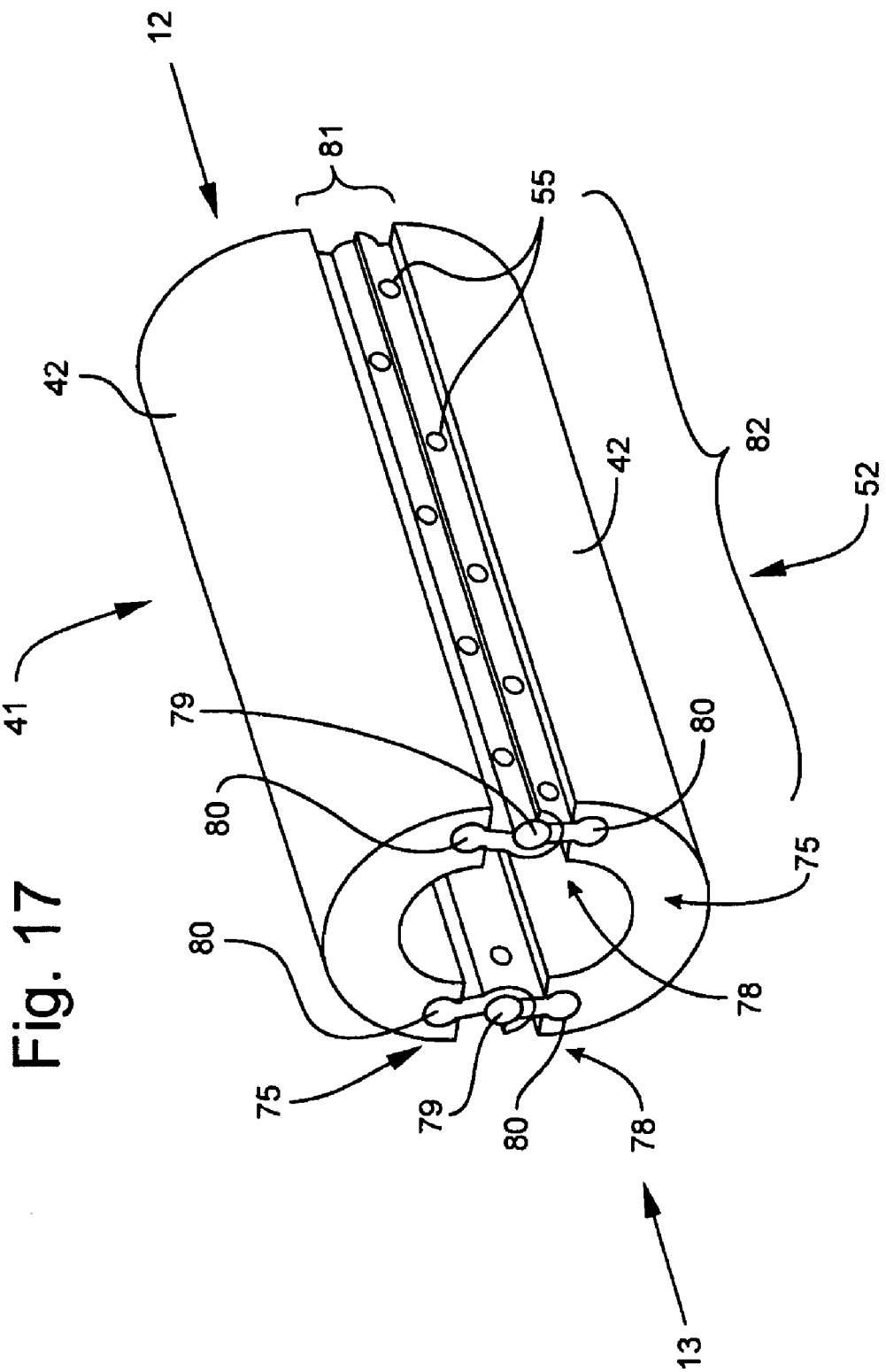
FIG. 17 is a perspective view of the outer expandable component comprising outer expandable members and two locking bridges shown in FIG. 16, in an embodiment of the present invention.

In the unexpanded configuration 51, the expandable members 42 can together define the lumen 45 of the outer expandable component 41 along the longitudinal axis 21 of the device 70. In some embodiments, the locking bridge 75 can be collapsed within the outer expandable component lumen 45, as shown in FIG. 15. The locking bridge 75 can be moved to a deployed, or activated, position between the outer expandable members 42 when the expandable members 42 are expanded. Once properly positioned in a desired location and directional orientation between bones, for example, within the intervertebral space 97, the outer expandable members 42 can be expanded outwardly with the expandable body 71. As the outer expandable members 42 are expanded outwardly, the locking bridge 75 can be moved to a position between the expanded outer expandable members 42, such that the locking bridge 75 locks the outer expandable members 42 in the expanded configuration 52, as shown in FIGS. 16 and 17.

In some embodiments of the bone fusion device 70, the outer expandable members 42 can be expanded such that selected ones of the expandable members 42 contact adjacent bones, for example, the adjacent vertebral bodies 96. As an example, when first and second outer expandable members 42 are expanded outwardly, the first outer expandable member 42 can contact the upper vertebral body 96 and the second outer expandable member 42 can contact the lower vertebral body 96. In this expanded configuration 52, the locking bridge 75 can be locked in a straight, or substantially vertical, position between the upper and lower vertebral bodies 96. That is, the deployed locking bridge 75 can be substantially perpendicular to the plane of the adjacent vertebral body endplates 93, and lock the outer expandable members 42 in the expanded configuration 52 against the endplates 93 of the adjacent vertebral bodies 96.

In some embodiments of the bone fusion device 70, the geometry of the locking bridge 75 and how the locking bridge connects to interfacing sides 76 can vary. For example, as shown in FIG. 15, the locking bridge 75 can include a pivotable flange 81 of material connected to each of the interfacing sides 76 along the length 82 of the outer expandable component 41. In the unexpanded configuration 51, the pivotable flange 81 can extend into the lumen 45 of the outer expandable component 41. As shown in FIG. 17, the pivotable flange 81 can unfold, or pivot, along the length 82 of the expandable component 41 such that the flange 81 extends between the two expandable members 42 in the expanded configuration 52. In some embodiments, the pivotable flanges 81 can include a plurality of bone growth openings 55 to allow contact of bone growth promotion material inside the lumen 45 with the vertebral bodies 96 to facilitate in-growth of a bone fusion mass between the vertebral bodies 96. Certain embodiments of the locking bridge 75 can further include a terminal locking arm 78 at each of the proximal and distal ends 12, 13, respectively, of the pivotable flange 81. The locking arm 78 can be connected to the ends of adjacent outer expandable components 42 with an anchor arm 80 fixed to the end of each expandable member 42. The locking arm 78 can articulate about a pivot connector 79 disposed between the anchor arms 80. The pivot connector 79 can be connected at the pivot point to the end of the locking bridge pivotable flange 81 so that the locking arm 78 can pivot in conjunction with the pivotable flange 81.

In particular embodiments, when the expandable members 42 are fully expanded into the expanded configuration 52, the pivotable flange 81 and/or the locking arm 78 can lock in position so as to prevent the expandable members 42 from moving from that configuration 52. For example, the pivotable flange 81 and/or the locking arm 78 can include a locking pin and receptacle combination (not shown) or can be configured structurally so that once pivoted into the fully expanded state 52, the pivotable flange 81 and/or the locking arm 78 can snap or lock into an unmovable position. In certain embodiments, the locking bridge 75 can be self-locking, such that moving the locking bridge 75 into the fully expanded position is sufficient (without further manipulation) to engage the locking bridge 75 and maintain the expandable members 42 in the expanded configuration 52.

Some embodiments of the bone fusion device 70 having the outer expandable component 41 can be delivered to the surgical site using the delivery cannula, or tube 72, in a minimally invasive manner. In some embodiments, the proximal end 12 of the outer expandable component 41 can be detachably attached to the distal end 13 of the delivery cannula 72. The outer expandable component 41 can be detachably attached to the delivery cannula 72 in various ways. For example, the proximal end 12 of the outer expandable component 41 and the distal end 13 of the delivery cannula 72 can be matingly threaded for detachable attachment to each other. In certain embodiments, the delivery tube 72 can be a separate tube independent from a catheter tube 73 for introducing the expandable body 71, as shown in FIGS. 14 and 16. In other embodiments, the delivery tube 72 can comprise the catheter tube 73 attached to the expandable body 71. When the outer expandable component 41 is properly positioned in the intervertebral space 97, the delivery cannula 72 can be detached, for example, by unthreading the cannula 72, from the outer expandable component 41.

Some embodiments of the bone fusion device 70 having the outer expandable component 41 can include a hydraulic mechanism for expanding the outer expandable members 41. Such a hydraulic mechanism can be the expandable body 71, for example, an inflatable balloon tube (not shown). The expandable body 71 can be inserted into the outer expandable component 41 positioned between the endplates 93 of two adjacent vertebrae 96 in the collapsed, or unexpanded, condition 51 in a minimally invasive manner. Such an expandable body 71 and minimally invasive procedures for inserting and expanding the expandable body 71 are further described and shown in co-pending U.S. patent application Ser. No. 11/177, 666, which is incorporated herein by reference in its entirety. In some embodiments of the present invention, for example, the expandable body 71 can be attached to the distal end 13 of the catheter tube 73. The catheter tube 73 can be introduced through the lumen of the delivery cannula 72, and the expandable body 71 positioned within the outer expandable members 42. Delivery and positioning of the expandable body 71 can be monitored using radiologic or CT visualization.

The catheter tube 73 can comprise material(s) that provide a balance of rigidity and flexibility to facilitate delivery and manipulation of the expandable body 71 through the delivery cannula 72 and within the outer expandable members 42. Such materials can include, for example, vinyl, nylon, polyethylenes, ionomer, polyurethane, and polyethylene tetraphthalate (PET), stainless steel, Kevlar™ material, PEBAX™ material, nickel-titanium alloys (Nitinol™ material), and other metal alloys. The expandable body 71 can comprise material(s) that allow expansion with a fluid or gas so as to expand the outer expanding component 41 into the expanded configuration 52. Such materials can include, for example, medical grade plastics like vinyl, nylon, polyethylenes, ionomer, polyurethane, and polyethylene tetraphthalate (PET). Such material(s) can be selected to exhibit generally elastic properties, like latex, or less elastic properties, like silicone.

In certain embodiments, the expandable body 71 can be sized such that its length is equivalent to the length 82 of the outer expandable component 41. When the same-length expandable body 71 is centered within the lumen 45 of the outer expandable component 41, the expandable members 42 can be expanded uniformly along the length 82 of the expandable component 41. In other embodiments, the expandable body 71 can have a length less than the length 82 of the outer expandable component 41, which may be useful for expanding only one end of the expandable component 41 to create a tapered expanded configuration 52 that matches the normal spinal curvature, for example.

The catheter tube 73 can include an interior lumen (not shown), and the lumen can be coupled at the proximal end 12 of the catheter tube 73 to a source of fluid via a fluid port 74. The lumen can convey the fluid into the expandable body 71 to cause it to expand. The fluid can be radiopaque so that expansion of the expandable body 71 can be monitored fluoroscopically or under CT visualization. Expansion of the expandable body 71 exerts pressure directly against the outer expandable members 42, causing the expandable members 42 to expand outwardly away from each other and into the expanded configuration 52 against the adjacent vertebral bodies 96.

Certain embodiments can include an indicator mechanism to indicate when the expandable body 71 is fully inflated and/or the outer expandable members 42 are in the fully expanded configuration, or position 52. For example, components of the bone fusion device 70, such as the outer expandable members 42 and/or the expandable body 71 can include radiopaque indicators, and the procedure can be visualized under fluoroscopy. Alternatively, or in addition, the expandable balloon 71 may have an end-volume inflation indicator, and/or the locking bridge 75 can include an audible indicator when the bridge 75 moved into the locked position.

As shown in FIG. 20, once the intervertebral disc 94 has been removed, the vertebral bodies 96 can become misaligned. When the outer expandable members 42 are expanded into the expanded configuration 52, the vertebrae 96 can be shifted back into, or near, normal alignment with each other, as shown in FIG. 21.

Once the outer expandable members 42 have been expanded and secured in position against the vertebral bodies 96 with the locking bridge 75, the expandable body 71 can be re-collapsed by withdrawing the fluid from the expandable body 71 through the catheter tube 73 lumen. In embodiments in which the expandable body 71 and the catheter tube 73 are separate from the bone fusion device delivery tube 72, the catheter tube 73 and the expandable body 71 can be removed from the surgical site by retracting the catheter tube 73 and the expandable body 71 through the delivery tube 72.

When embodiments of the bone fusion device 70 are utilized in spinal fusion, the adjacent vertebral bodies 96 can transmit a significant compressive force onto the outer expandable members 42 in the intervertebral space 96. The expandable body, or balloon 71, can be capable of sufficient expansion force to overcome such compressive force and to expand the outer expandable members 42 into the expanded and deployed configuration 52. In certain embodiments, the expandable body 71 can be capable of sufficient expansion force to distract the endplates 93 of adjacent vertebrae 96.

In certain embodiments, the expandable body 71 can comprise sufficient mechanical advantage, or expansibility advantage, to overcome the compressive forces transmitted from the adjacent vertebral bodies 96. In such embodiments, the expandable body 71 can be utilized to force apart the endplates 93 of the vertebral bodies 96 as the outer expandable members 42 are being expanded outwardly.

In some embodiments, the locking bridge 75 can lock the outer expandable members 42 into position with each other when the expandable members 42 are deployed into the fully expanded configuration 52. That is, in such embodiments, the outer expandable component 41 can be moveable between the unexpanded configuration 51 and the expanded configuration 52 without intermediate locking positions, such that the locking bridge 75 is not lockable in less than the fully expanded position 52.

In other embodiments, the outer expandable members 42 can be expanded in increments of expansion between the unexpanded configuration 51 and the fully expanded configuration 52. In such embodiments, the bone fusion device 70 can include a mechanism by which the outer expandable members 42 can be locked into position with each other when the outer expandable members 42 have been expanded to those incremental positions of expansion. For example, the outer expandable members 42 may be expanded to first, second, and third increments of expansion, and the locking bridge 75 can be locked at corresponding first, second, and third incremental locking positions. In such embodiments, the locking bridge 75 may comprise a ratchet-type incremental locking system. In this way, the surgeon can select the desired degree of expansion in a particular patient. Alternatively, some embodiments can include various sizes of the expandable body 71 that may be used to expand the outer expandable members 42 outwardly a predetermined amount to a selected incremental position of expansion and locking.

Embodiments of the bone fusion device 70 having the outer expandable component 41 and the locking mechanism can comprise various suitable biocompatible materials as described herein. In some embodiments of the bone fusion device 70, the locking bridge 75 can lock the outer expanding members 42 in the expanded configuration 52 for the functional life of the device 70. The material(s) in both the locking bridge 75 and the outer expanding members 42 can have sufficient tensile strength to maintain the device 70 in the expanded configuration 52 under the loads placed on the device 70 by the compressive force transmitted by the vertebrae 96. In certain embodiments, the bone fusion device 70 can comprise materials that are radiolucent so that a developing fusion mass within the device 70 can be seen under traditional radiographic visualization techniques and in CT scans without enhancement techniques.

In certain embodiments, the fusion device 70 having the outer expandable component 41 and the locking mechanism can include walls having various thicknesses. The thickness of the walls of the outer expandable members 42 can be selected depending on factors such as size of access route and the desired dimensions of the expanded configuration 52. The overall unexpanded dimensions of such a bone fusion device 70 can depend on, for example, a desired expanded configuration 52 for restoring the normal height of the intervertebral disc space 97. In certain embodiments, the outer surface of the outer expandable members 42 can be varied in order to optimize interaction with the adjacent vertebral bodies 96 and to prevent movement of the device 70 following implantation.

Such embodiments of the bone fusion device 70 having outer expandable members 42 that can be self-locking upon deployment have advantages over conventional bone fusion devices. For example, the outer expandable members 42 can be inserted in the collapsed, or unexpanded, configuration 51 into a space between bones, thereby allowing insertion using a minimally invasive surgical procedure. Such a device 70 can engage adjacent bones, such as vertebral bodies 96, in such a manner as to be self-stabilizing. As a result, such embodiments provide for maintaining appropriate intervertebral spacing and stabilization of the vertebrae 96 during the fusion process.

The present invention can include embodiments of a bone fusion system and/or a bone fusion device kit. Such a system and/or kit can include embodiments of the bone fusion device 70 as described herein. For example, the bone fusion device 70 can include the outer expandable component 41 comprising a plurality of outer expandable members 42. Each outer expandable member 42 can cooperate in the unexpanded configuration 51 to define the lumen 45, and can have at least one separable interface 77 with another one of the outer expandable members 42 along the length 82 of the device 70. The device 70 can further include the locking bridge 75 at each interface 77 connecting each outer expandable member 42 with another one of the outer expandable members 42. The locking bridge 75 can be movable from the unexpanded configuration 51 to a locked expanded configuration 52. The device 70 can further include the expandable body 71, such as an inflatable balloon, insertable into the lumen 45 of the outer expandable component 41 and adapted to expand the outer expandable members 42 into the expanded configuration 52. When the outer expandable members 42 are expanded by the expandable body 71 into the expanded configuration 52, each locking bridge 75 can lock the expandable members 42 together.

In some embodiments of a bone fusion system and/or a bone fusion device kit, when each locking bridge 75 is locked in the expanded configuration 52 between adjacent vertebral body endplates 93, the locking bridge 75 can be substantially perpendicular to the endplates 93. In some embodiments, each locking bridge 75 can be independent from each other locking bridge 75. In particular embodiments of a system and/or kit, the locking bridge 75 may further include the pivotable flange 81 connected to the interface 77 between two of the outer expandable members 42 along the length 82 of the device 70. The flange 81 can be pivotable between the unexpanded configuration 51 and the expanded configuration 52. The locking bridge 75 may further include the terminal locking arm 78 having a center pivot connector 79 pivotably connected on each end of the pivotable flange 81 and the anchor arm 80 anchored to the end of each of the two outer expandable members 42. The locking arm 78 can be pivotable between the anchor arms 80, such that the flange 81 and the terminal locking arm 78 can self-lock in the expanded configuration 52.

Some embodiments of a bone fusion system and/or a bone fusion device kit of the present invention may further include, for example, a plurality of incrementally sized bone fusion devices 70, which can be selected by the surgeon based on the size needed for a particular patient. In some embodiments, systems and/or kits can include instrumentation for performing implantation of an embodiment of the bone fusion device 70 with or without a plurality of incrementally sized bone fusion devices 70.

The present invention can include embodiments of a method for fusing bone. Such a method can comprise utilizing the bone fusion device 70, system, and/or kit as described herein. For example, one such method can include providing the bone fusion device 70 including the outer expandable component 41 comprising a plurality of outer expandable members 42. Each outer expandable member 42 can cooperate in the unexpanded configuration 51 to define the lumen 45, and can have at least one separable interface 77 with another one of the outer expandable members 42 along the length 82 of the device 70. The device 70 can further include the locking bridge 75 at each interface 77 connecting each outer expandable member 42 with another one of the outer expandable members 42. The locking bridge 75 can be movable from the unexpanded configuration 51 to a locked expanded configuration 52.

The method can further include inserting the expandable body 71, such as an inflatable balloon, into the lumen 45 of the outer expandable component 41 and expanding the outer expandable members 42 into the expanded configuration 52. When the outer expandable members 42 are expanded by the expandable body 71 into the expanded configuration 52, each locking bridge 75 can lock the expandable members 42 together.

Some embodiments of the method can further include delivering the bone fusion device 70 to a target bone site, for example, the intervertebral space 97, in the compressed, or unexpanded, configuration 51. Accordingly, the unexpanded bone fusion device 70 can be delivered into the intervertebral space 97 utilizing a minimally invasive surgical procedure. Some embodiments of the method can further include providing each locking bridge 75 as independent from each other locking bridge 75. In certain embodiments, each locking bridge 75 can be locked in the expanded configuration 52 between adjacent vertebral body endplates 93 in a position substantially perpendicular to the endplates 93.

Embodiments of a bone fusion device, system, kit, and method of the present invention can be utilized for facilitating stabilization or fusion of bones. Some embodiments can be advantageously used in the stabilization and fusion of a joint, particularly an intervertebral joint 97. Embodiments have been described herein with reference to stabilization and fusion of adjacent vertebrae 96. Some embodiments may be applicable for use with various types of joints (for example, intervertebral, ankle, interdigital, etc.) and in various anatomical regions (for example, spine, arms, legs, etc.) of a human or animal body. In the spinal column 90, the devices and methods disclosed may be used at all intervertebral joints, including those in the cervical, thoracic, and lumbar region.

Although the present invention has been described with reference to particular embodiments, it should be recognized that these embodiments are merely illustrative of the principles of the present invention. Those of ordinary skill in the art will appreciate that a spinal fusion device, system, kit, and methods of the present invention may be constructed and implemented in other ways and embodiments. Accordingly, the description herein should not be read as limiting the present invention, as other embodiments also fall within the scope of the present invention.

What is claimed is:

1. A bone fusion device comprising:
    a plurality of elongated interlockable segments, each segment having at least a first side and a second side extending transversely to each other along a longitudinal axis of the segment, the segment including at least one longitudinal opening extending along the longitudinal axis and defining a hollow interior region of the segment;
    a first engaging surface along the first side; and
    a second mateably engaging surface along the second side,
    wherein the first engaging surface on a first one of the segments inserted into a location between bones is engageable with the second engaging surface on a second one of the segments inserted into the location so that the first and second segments are interlockable side by side in the location; and
    wherein the interlockable segments comprise separate individual elements entirely separable from one another and configured for individual insertion into the location between the bones and structured to be interlocked with one another in situ at the location between the bones by engagement of the first engaging surface with the second engaging surface.

2. The device of claim 1, wherein the first engaging surface further comprises a channel and the second engaging surface further comprises a rib matingly interlocked within the channel in situ at the location between the bones.

3. The device of claim 1, further comprising the longitudinal axis of the segments orientable perpendicularly to a vertical axis of a spinal column.

4. The device of claim 1, wherein each segment includes a plurality of transverse openings extending transversely from an outer surface of the segment and into communication with the at least one longitudinal opening.

5. The device of claim 4, further comprising a bone growth promoting material positioned within the at least one longitudinal opening to promote bone growth into the hollow interior region of the segment.

6. The device of claim 1, wherein the at least one longitudinal opening extends entirely through each segment; and
    further comprising a guide wire positioned within the at least one longitudinal opening and adapted to guide the segment to the location between the bones.

7. The device of claim 6, wherein each segment includes a plurality of transverse openings extending transversely from an outer surface of the segment and into communication with the at least one longitudinal opening.

8. The device of claim 1, further comprising two of the at least one longitudinal opening extending along the longitudinal axis and each defining a hollow interior region of the segment.

9. The device of claim 8, wherein each segment includes a plurality of transverse openings extending transversely from an outer surface of the segment and into communication with at least one of the longitudinal openings.

10. A bone fusion device comprising:
    a plurality of elongated interlockable segments, each segment having at least a first side and a second side extending transversely to each other along a longitudinal axis of the segment;
    a first engaging surface along the first side; and
    a second mateably engaging surface along the second side,
    wherein the first engaging surface on a first one of the segments inserted into a location between bones is engageable with the second engaging surface on a second one of the segments inserted into the location so that the first and second segments are interlockable side by side in the location; and
    a delivery tube detachably attachable to a proximal end of each of the segments, wherein the delivery tube comprises a size slightly larger than an outer dimension of a single segment such that the device can be delivered to the location utilizing a minimally invasive procedure; and
    a guide wire insertable through the delivery tube and through a longitudinal lumen extending along the longitudinal axis in the segment, the guide wire adapted to control a position of the first segment while the second segment is locked to the first segment.

11. A method for fusing bone, comprising:
    providing a bone fusion device comprising a plurality of interlockable segments;
    positioning a first one of the segments attached to a delivery tube in a location between bones;
    detaching the delivery tube from the first segment;
    attaching the delivery tube to a second one of the segments;
    positioning the second segment with the delivery tube in the location adjacent the first segment;
    interlocking the first and second segments in the location; and
    detaching the delivery tube from the second segment;
    each segment having a guide wire lumen, the method further comprising:

inserting a first guide wire through the delivery tube and a guide wire lumen in the first segment; and inserting a second guide wire through the delivery tube and a guide wire lumen in the second segment, wherein interlocking the first and second segments further comprises controlling the position of the first segment in the location with the guide wire while the first and second segments are being interlocked.

12. A bone fusion device comprising:

an outer expandable component having a plurality of outer expandable members each having a length extending along a longitudinal axis of the outer expandable component, the outer expandable component insertable to a location between bones in an unexpanded configuration;

an inner expander movable from a proximal end toward a distal end of the outer expandable component to expand the outer expandable members into an expanded configuration;

inner surface engaging portions in the outer expandable members; and outer surface engaging portions on the inner expander matingly engageable and interlockable with the inner surface engaging portions in the outer expandable members in the expanded configuration to limit displacement of the outer expandable members away from the inner expander; and wherein each of the outer expandable members are interlocked with the inner expander by a locking rib that is matingly interlocked within a locking channel to retain the outer expandable members on the inner expander, and wherein the locking rib and the locking channel each have a length extending along the longitudinal axis of the outer expandable component whereby relative axial displacement of the locking rib within the locking channel in a direction along the longitudinal axis expands the outer expandable members into the expanded configuration.

13. The device of claim 12, wherein the outer expandable members comprise separate individual elements that are entirely separable from one another and which are each individually interlocked with the inner expander.

14. The device of claim 12, wherein expansion of the outer expandable members by the inner expander comprises uniform expansion along a longitudinal axis of the outer expandable members to provide the outer expandable component with a substantially uniform height.

15. A bone fusion device comprising:

an outer expandable component having a plurality of outer expandable members each having a length extending along a longitudinal axis of the outer expandable component, the outer expandable component insertable to a location between bones in an unexpanded configuration;

an inner expander movable from a proximal end toward a distal end of the outer expandable component to expand the outer expandable members into an expanded configuration;

inner surface engaging portions in the outer expandable members; and outer surface engaging portions on the inner expander matingly engageable and interlockable with the inner surface engaging portions in the outer expandable members in the expanded configuration to limit displacement of the outer expandable members away from the inner expander; and wherein the outer expandable members are separable from each other in a radial direction relative to the longitudinal axis and cooperate with one another to provide the expanded configuration of the outer expandable members with a circular outer cross section along the longitudinal axis.

16. A bone fusion device comprising:

an outer expandable component having a plurality of outer expandable members insertable to a location between bones in an unexpanded configuration;

an inner expander movable from a proximal end toward a distal end of the outer expandable component to expand the outer expandable members into an expanded configuration;

inner surface engaging portions in the outer expandable members; and outer surface engaging portions on the inner expander matingly engageable and interlockable with the inner surface engaging portions in the outer expandable members in the expanded configuration to limit axial displacement of the outer expandable members away from the inner expander;

wherein each of the outer expandable members are interlocked with the inner expander by a locking rib that is matingly interlocked within a locking channel to retain the outer expandable members on the inner expander;

an inner rod detachably attached to the outer expandable component; and a pushing tube detachably attached to the inner expander, wherein the inner expander and the attached pushing tube are slidable about the inner rod so that a distal end of the inner expander is engageable with the outer expandable component.

17. A bone fusion device comprising:

an outer expandable component having a plurality of outer expandable members each having a length extending along lonitudinal axis of the outer expandable component, the outer expandable component insertable to a location between bones in an unexpanded configuration;

an inner expander movable from a proximal end toward a distal end of the outer expandable component to expand the outer expandable members into an expanded configuration;

inner surface engaging portions in the outer expandable members; and outer surface engaging portions on the inner expander matingly engageable and interlockable with the inner surface engaging portions in the outer expandable members in the expanded configuration to limit displacement of the outer expandable members away from the inner expander; and wherein the outer surface engaging portions further comprise a plurality of locking flanges extending outwardly from the outer surface of the inner expander, and wherein the inner surface engaging portions in each of the outer expandable members further comprises a locking channel configured to matingly interlock with one of the locking flanges, and wherein the locking flanges and the locking channels each have a length extending along the longitudinal axis of the outer expandable component whereby relative axial displacement of the locking flanges within the locking channels in a direction along the longitudinal axis expands the outer expandable members into the expanded configuration.

18. A bone fusion device comprising:

an outer expandable component comprising a plurality of outer expandable members, each outer expandable member including a number of engaging surfaces positioned in engagement with one or more engaging surfaces of at least one other outer expandable member along at least one separable interface in an unexpanded configuration to define a lumen;

a locking bridge at each interface connecting each outer expandable member with another one of the outer expandable members and movable from the unexpanded configuration to a locked expanded configuration where each of the engaging surfaces is disengaged from the one or more engaging surfaces of the at least one other outer expandable member; and an expandable body insertable into the lumen of the outer expandable component and adapted to expand the outer expandable members into the expanded configuration, wherein in the expanded configuration each locking bridge locks the outer expandable members together.

19. The device of claim 18, wherein each locking bridge locked in the expanded configuration between adjacent vertebral body endplates is substantially perpendicular to the endplates.

20. The device of claim 18, wherein each locking bridge is independent from each other locking bridge.

21. The device of claim 18, wherein the locking bridge further comprises:

a flange connected to the interface between two of the outer expandable members along a length of the device and pivotable between the unexpanded configuration and the expanded configuration; and a terminal locking arm having a center pivot connector pivotably connected on each end of the pivotable flange and an anchor arm anchored to the end of each of the two outer expandable members, the locking arm pivotable between the anchors, wherein the flange and the terminal locking arm self-lock in the expanded configuration.

22. The device of claim 18, wherein the outer expandable members comprise separate individual elements that are entirely separable from one another and which are locked in the expanded configuration by the locking bridge at each interface location.

23. A method for fusing bone, comprising:

providing a bone fusion device comprising an outer expandable component comprising a plurality of outer expandable members, each outer expandable member including a number of engaging surfaces positioned in engagement with one or more engaging surfaces of at least one other outer expandable member along at least one separable interface in an unexpanded configuration to define a lumen;

inserting an expandable body into the outer expandable component;

expanding the expandable body to expand the outer expandable members into an expanded configuration where each of the engaging surfaces is disengaged from the one or more engaging surfaces of the at least one other outer expandable member; and the device further comprising a locking bridge at each interface connecting each outer expandable member with another one of the outer expandable members, the method further comprising moving each locking bridge from the unexpanded configuration to a locked expanded configuration to lock the outer expandable members together.

24. The method of claim 23, wherein moving each locking bridge from the unexpanded configuration to an expanded configuration further comprises moving each locking bridge to the expanded configuration between adjacent vertebral body endplates such that each locking bridge is substantially perpendicular to the endplates.

25. The method of claim 23, wherein the outer expandable members comprise separate individual elements that are entirely separable from one another and which are locked in the expanded configuration by the locking bridge at each interface location.

* * * * *